United States Patent
Paek et al.

(10) Patent No.: US 9,592,262 B2
(45) Date of Patent: Mar. 14, 2017

(54) COMPOSITION FOR PREVENTING OR TREATING HANGOVER

(71) Applicant: CJ CHEILJEDANG CORPORATION, Seoul (KR)

(72) Inventors: Se Hee Paek, Seoul (KR); Byoung Seok Moon, Gyeonggi-do (KR); Seok Jun Park, Seoul (KR); Yong Ki Seo, Seoul (KR); Geun Seog Song, Seoul (KR)

(73) Assignee: CJ CHEILJEDANG CORPORATION (KR)

( * ) Notice: Subject to any disclaimer, the term of this patent is extended or adjusted under 35 U.S.C. 154(b) by 0 days.

(21) Appl. No.: 14/255,838

(22) Filed: Apr. 17, 2014

(65) Prior Publication Data
US 2014/0314887 A1    Oct. 23, 2014

(30) Foreign Application Priority Data

Apr. 18, 2013 (KR) .......................... 10-2013-0043222

(51) Int. Cl.
| | |
|---|---|
| *A61K 36/54* | (2006.01) |
| *A61K 36/33* | (2006.01) |
| *A61K 36/738* | (2006.01) |
| *A61K 36/52* | (2006.01) |
| *A61K 36/72* | (2006.01) |
| *A23L 2/52* | (2006.01) |
| *A61K 36/62* | (2006.01) |

(52) U.S. Cl.
CPC ................ *A61K 36/54* (2013.01); *A23L 2/52* (2013.01); *A23L 33/105* (2016.08); *A61K 36/33* (2013.01); *A61K 36/52* (2013.01); *A61K 36/62* (2013.01); *A61K 36/72* (2013.01); *A61K 36/738* (2013.01)

(58) Field of Classification Search
None
See application file for complete search history.

(56) References Cited

U.S. PATENT DOCUMENTS

2011/0268718 A1* 11/2011 Rauchdobler .......... A61K 36/33
 424/94.1
2011/0280977 A1* 11/2011 Park ...................... A23L 1/3002
 424/765

FOREIGN PATENT DOCUMENTS

| JP | 2000-344675 A | 12/2000 |
|---|---|---|
| JP | 2008-540404 | 11/2008 |
| JP | 2011-225565 | 11/2011 |
| KR | 1020040094173 A | 11/2004 |
| KR | 100828708 | 5/2008 |
| KR | 1020110115862 A | 10/2011 |
| RU | 2129008 | 4/1999 |
| RU | 2327482 | 6/2008 |

OTHER PUBLICATIONS

English translation for Kawahara—JP 2000344675 A—Dec. 2000.*
Tinoco et al., "Effects of a hexane extract from Laurus novocanariensis leaves on the ethanol metabolism of Wistar rats," Fitoterapia 80: 130-133, 2009.
Yoshikawa et al., "Alcohol Absorption Inhibitors from Bay Leaf (*Laurus nobilis*): Structure-Requirements of Sesquiterpenes for the Activity," Bioorganic & Medicinal Chemistry 8: 2071-2077, 2000.
Kak ustranit pokhmelnyi sindrom, Data list [on-line] May 25, 2012. (Found Dec. 10, 2014 in Internet: http://frend.org.ua/post221572885/, 1 page.
Matsuda, et al., "Preventive effect of sesquiterpenes from bay leaf on blood ethanol elevation in ethanol-loaded rat: structure requirement and suppression of gastric emptying," Bioorg. Med. Chem. Lett. 9(18):2647-52 (1999).
Phytochai "Dionisii" Data list [on-line] Apr. 29, 2011 (found Dec. 10, 2014, http://www.zn-fito.ru/stati/id35, 2 pages.
Russian Office Action, for RU Application 2014115500/15, received on Dec. 22, 2014. 6 pages.
Wiese, et al., "Effect of Opuntia ficus indica on symptoms of the alcohol hangover," Arch. Intern. Med. 164(12):1334-40 (2004).

* cited by examiner

*Primary Examiner* — Susan Hoffman
(74) *Attorney, Agent, or Firm* — Cooley LLP

(57) ABSTRACT

The present invention relates to a composition including a *Laurus nobilis* leaf extract as an active ingredient, and particularly, to a composition for preventing or treating hangover including the *Laurus nobilis* leaf extract, a food composition for preventing or relieving hangover including the *Laurus nobilis* leaf extract, and a method for preparing the composition. Since the composition according to the present invention includes the *Laurus nobilis* leaf extract, it has a remarkably excellent effect of lowering blood concentrations of alcohol and acetaldehyde. Its hangover-preventing and treating effects were confirmed by behavioral tests, and thus the composition can be widely applied to foods, drugs, or functional health foods which can be effectively used for preventing and treating hangover.

5 Claims, 24 Drawing Sheets

COMPOSITION FOR PREVENTING OR TREATING HANGOVER

CROSS REFERENCE TO RELATED APPLICATION

This application claims priority to Korean Patent Application No. 10-2013-0043222, filed Apr. 18, 2013, which is incorporated by reference in its entirety.

TECHNICAL FIELD

The present invention relates to a composition comprising a *Laurus nobilis* leaf extract as an active ingredient, and particularly, to a composition for preventing or treating hangover comprising a *Laurus nobilis* leaf extract, a food composition for preventing or relieving hangover comprising a *Laurus nobilis* leaf extract, and a method for preparing the composition.

BACKGROUND ART

Alcohol has occupied an important place in the history of humankind for at least 8000 years. However, as system for improved sanitation and water purification were introduced in the 1800s, its value as a food decreased and the use of alcoholic beverages shifted towards their present day role as a socially acceptable form of recreation with alcoholic beverages having a higher concentration of alcohol. In 2005, each Korean consumed on average 97 bottles of soju (8.11 liters of alcohol), and the consumption is increasing every year despite the development of the country.

Like other sedative-hypnotic drugs, a small amount of alcohol relieves anxiety and fosters a feeling of being comfortable. However, alcohol is the most commonly abused material in the world and it is the major cause of vast medical and societal costs. In Korean, economic loss for society due to drinking has already exceeded an estimated 20 trillion won, which accounts for more than 3% of the gross domestic product (GDP).

Contemporary people are exposed to a variety of stress and the extent of the stress is gradually increasing. To escape such stress, different activities such as exercise, sleeping, smoking, traveling, etc. are conducted. Drinking (alcohol consumption) in an attempt to relieve stress is the most popular method.

In particular, as society becomes more complex and organized, frequent drinking habits are prevailing, and heavy drinking and binge drinking continue to rise. Such drinking affects occupational performance of many people the next day, and consequently, a long-term drinking habit causes health problems.

Hangover indicates unpleasant physical and mental symptoms after drinking alcohol, and its objective symptoms include headache, nausea, vomiting, sleepiness, lowering of capacity for locomotion, hematological change and change in hormones. The cause for hangovers is still unclear, but is known to be metabolic products of alcohol metabolism.

Ethyl alcohol introduced into the body is absorbed by the stomach or the small intestine, and is transferred to the liver through blood vessels. Liver cells have alcohol dehydrogenase (ADH) which oxidizes alcohol to produce acetaldehyde. Acetaldehyde is metabolized to produce acetic acid by acetaldehyde dehydrogenase (ALDH) in liver cells and is transferred to muscles or fat tissue throughout the whole body, and is finally decomposed to carbon oxide and water.

In addition, the acetaldehyde dehydrogenase is divided into type II, which initiates oxidation even in a low concentration of acetaldehyde, and type I, which only functions in a high concentration of acetaldehyde. Since Eastern people are generally deficient in type II acetaldehyde dehydrogenase, the oxidation of acetaldehyde is slower in Eastern people than in Western people. Non-oxidized acetaldehyde and/or ethanol interfere with the normal metabolism, thereby causing various hangover symptoms.

Due to the social background of Korean drinking culture, there is a continuous demand for products which can relieve hangover. Many studies have been done to reduce hangover, and actually, many different products that are commercially available have been newly introduced in the market.

However, most products are unsatisfactory because objective verification of the efficacy of the actual final products is still lacking. In fact, the confidence in the product of consumers in need of hangover relief drinks is generally low. Accordingly, there is an urgent need to develop a product that exhibits hangover relief efficacy so as to gain consumer confidence when consumers actually drink the product, reduces the social impact due to excessive drinking, and helps people achieve a healthy life.

DISCLOSURE

Technical Problem

Under this background, the present inventors have made many efforts to provide a drink that is effective in hangover relief. As a result, they found that a composition including a *Laurus nobilis* leaf leaf extract is able to rapidly lower blood concentrations of alcohol and acetaldehyde, and they also confirmed its hangover relief effect of reducing the aftereffect of hangover through animal behavioral studies, thereby completing the present invention.

Technical Solution

An object of the present invention is to provide a composition for preventing or treating hangover comprising a *Laurus nobilis* leaf extract as an active ingredient.

Another object of the present invention is to provide a food composition for preventing or relieving hangover comprising the *Laurus nobilis* leaf extract as an active ingredient.

Still another object of the present invention is to provide a method for preparing the *Laurus nobilis* leaf extract; and the composition of the present invention.

Advantageous Effects

The composition according to the present invention comprises a *Laurus nobilis* leaf extract to exhibit remarkably excellent effects of lowering blood concentrations of alcohol and acetaldehyde, and such hangover-preventing and treating effects were confirmed by behavioral studies. Therefore, the composition can be widely applied in foods, drugs, or functional health foods which could be effectively used for preventing and treating hangover.

BEST MODE

Figure 1:
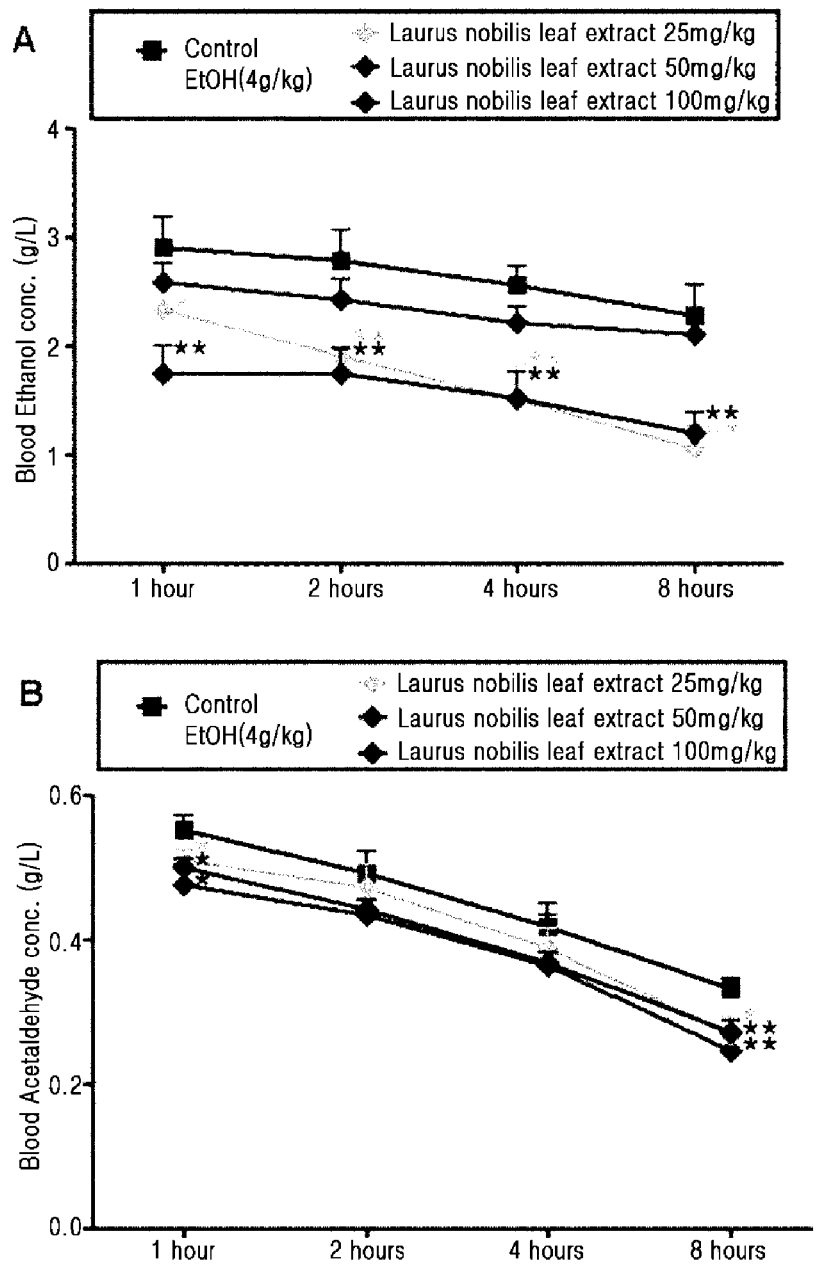
FIG. 1 is a graph showing (A) blood alcohol concentration and (B) blood acetaldehyde concentration of the alcohol-treated animals, after treatment of a control group (non-*Laurus nobilis* leaf extract-treated group; EtOH-treated group) and an experimental group (*Laurus nobilis* leaf extract-treated group) (Mean±SEM, n=8/*p<0.05 and ** p<0.001 versus EtOH-treated group)

In one aspect to achieve the above objects, the present invention provides a composition for preventing or treating hangover comprising a *Laurus nobilis* leaf extract as an active ingredient.

The composition of the present invention may preferably further comprise an *Opuntia ficus* indica extract so as to be a composition comprising the *Laurus nobilis* leaf extract and the *Opuntia ficus* indica extract, and more preferably, further comprise a *Rosa roxburghii* extract so as to be a composition comprising the *Laurus nobilis* leaf extract, the *Opuntia ficus* indica extract, and the *Rosa roxburghii* extract. Most preferably, the composition may be a composition comprising the *Laurus nobilis* leaf extract, the *Opuntia ficus* indica extract, the *Rosa roxburghii* extract, an *Engelhardtia chrysolepis* HANCE extract, and a *Nelumbo nucifera* seed extract.

In order to discover a substance showing an efficacy on relieving hangover, the present inventors have studied the effect of lowering blood concentrations of alcohol and acetaldehyde for various substances. As a result, the present inventors found that blood concentrations of alcohol and acetaldehyde can be remarkably lowered by a composition with addition of the *Opuntia ficus* indica extract and the *Laurus nobilis* leaf extract to the conventional mixture comprising *Rosa roxburghii* extract. This mixture known to have the effect of lowering a concentration of alcohol or acetaldehyde, a cause of hangover, can be used as a food or drug for preventing, relieving or treating hangover.

As used herein, the term "*Laurus nobilis*" is an evergreen shrub belonging to the family Lauraceae and the order Ranunculales, and the *Laurus nobilis* leave is known to have diuretic, digestive and anticancer functions. Generally, fresh or dried leaves of *Laurus nobilis* are used for flavoring in cooking. Meanwhile, it is known that oil obtained from the *Laurus nobilis* leaves is used in the preparation of antimicrobial agents and pesticides for agriculture, and oil obtained from the *Laurus nobilis* fruits is effective for bruise or strain. There is no report that the *Laurus nobilis* leave is effective in hangover relief, and such use has been first demonstrated by the present inventors. In one embodiment of the present invention, the *Laurus nobilis* leaf extract was prepared using the leaves of *Laurus nobilis*.

As used herein, the term "*Opuntia ficus* indica" is the fruit of *Opuntia ficus* indica growing wild in Jeju Island, and is rich in dietary fiber and minerals such as calcium and iron. *Opuntia ficus* indica has been used for treatment of fevers, bronchial asthma, indigestion, stomach cramps, constipation, heartburn, poor blood circulation, etc., and has high content of vitamin C. In recent years, it has been known that *Opuntia ficus* indica contains high levels of polyphenols to inhibit hypertension, cancer, aging, etc.

As used herein, the term "*Rosa roxburghii*" is, also called sweet chestnut rose, a plant belonging to the family Rosaceae, and widely distributed throughout East Asia, China and Himalayas, etc., and fruits and seeds thereof are edible. It contains abundant vitamins or the like, and has high SOD (superoxide dismutase) activity to have antioxidant functions.

As used herein, the term "*Engelhardtia chrysolepis* HANCE" is a plant belonging to the family Juglandaceae, and generally called "Taiwan engelhardtia". *Engelhardtia chrysolepis* HANCE is a drug commonly used in oriental medicine, and shows remarkable effects in excitement of the central nervous system and diuretic effect. *Engelhardtia chrysolepis* HANCE also inhibits nephritis, and retards progression of albuminuria and cholesterolemia. Its hypotensive effect was also recognized.

As used herein, the term "*Nelumbo nucifera*" is a plant known by numerous common names including Indian lotus, sacred lotus, bean of India, or simply lotus, and is one of two species of aquatic plant in the family Nelumbonaceae. *Nelumbo nucifera* seed is used as a medicine that is dried after removing the seed coat. *Nelumbo nucifera* seed is known to be non-toxic, have nutrition and tonic effects, and be effective for insomnia, chronic diarrhea, and loss of appetite.

As used herein, the "extract" may be prepared by extracting the powder of each plant using water, alcohol having 1 to 6 carbon atoms, preferably alcohol having 1 to 4 carbon atoms, or a mixture thereof as a solvent, and preferably, it may be extracted at 25° C. to 120° C. for 1 hr to 8 hours by cold immersion extraction, hot water extraction, ultrasonic extraction, reflux cold extraction, ultrahigh pressure extraction or heating extraction. However, as long as the method is used to extract a substance showing prophylactic or therapeutic effect on hangover, it is not particularly limited to the type thereof. The product undergone the extraction process is sequentially subjected to filtration, concentration under reduced pressure, and drying process, and thus prepared as the extract of the present invention. However, it is not particularly limited thereto, and the extract of the present invention includes all of a liquid extract, a diluted or concentrated liquid of the liquid extract, a dry extract prepared by drying the liquid extract, or a crude purified extract or a purified extract thereof. In addition, the extract may be extracted from various organs of natural plants, hybrids thereof or variants thereof.

In the present invention, an extract of *Laurus nobilis* leaf, *Opuntia ficus* indica, *Rosa roxburghii*, *Engelhardtia chrysolepis* HANCE, *Hovenia dulcis* fruit and *Nelumbo nucifera* seed (lotus) may be a powder extract prepared by extracting each herb medicine or a mixture thereof with water, ethanol, methanol, or a mixed solvent thereof, and then spray-drying the extract, but is not limited thereto.

The composition for preventing or treating hangover which is effective for hangover relief may have more effective prophylactic and therapeutic effects on hangover when the *Laurus nobilis* leaf extract, the *Opuntia ficus* indica extract, and the *Rosa roxburghii* extract are included in a weight ratio of 0.25 to 1:0.5 to 2:0.5 to 2.

As used herein, the term "hangover" indicates unpleasant physical and mental symptoms after drinking alcohol, and its objective symptoms include headache, nausea, vomiting, sleepiness, lowering of capacity for locomotion, hematological change and change in hormone. The cause of hangover is still unclear, but generally known to be highly associated with acetaldehyde which is a metabolic product of alcohol metabolism. That is, it is known that hangover generally occurs when the concentration of acetaldehyde remaining in the body is high.

As used herein, the term "prevention" refers to all of the actions by which occurrence of hangover is restrained or retarded by administration of a pharmaceutical composition for preventing or treating hangover including the composition according to the present invention. As used herein, the term "treatment" or "relief" refers to all of the actions by which the symptoms of hangover have taken a turn for the better or been modified favorably by administration of a pharmaceutical composition for preventing or treating hangover or a food composition for preventing or relieving hangover which includes the composition according to the present invention.

The composition for preventing or treating hangover of the present invention may have any one formulation selected from the group consisting of a tablet, a pill, a powder, granule, a capsule, a suspension, a liquid for internal use, an emulsion, a syrup, a sterilized aqueous solution, a non-aqueous solvent, a lyophilized preparation, and a suppository, and the composition may be prepared in a variety of oral or parenteral formulations. For formulations, a typical diluent or excipient, such as a filler, a bulking agent, a binder, a wetting agent, a disintegrating agent, or a surfactant, may be used. Examples of a solid formulation for oral administration include tablets, pills, powder, granules, and capsules, and these solid formulations are prepared by mixing one or more compounds with at least one excipient, for example, starch, calcium carbonate, sucrose, lactose, gelatin or the like. In addition to the simple excipient, a lubricant, such as magnesium stearate, talc or the like, is used. As a liquid formulation for oral administration, a suspension, a liquid for internal use, an emulsion, a syrup or the like may be used, and in addition to water and liquid paraffin, which is often used as the simple diluent, various other excipients, for example, a wetting agent, a sweetener, a flavoring agent, a preserving agent or the like may be included. As a formulation for parenteral administration, a sterilized aqueous solution, a non-aqueous solvent, a suspension, an emulsion, a lyophilized preparation, a suppository or the like may be used. For a non aqueous solvent or a suspension, propylene glycol, polyethylene glycol, a plant oil such as olive oil, an injectable ester such as ethylolate or the like may be used. As a base for suppositories, witepsol, macrogol, tween 61, cacao butter, laurin butter, glycerogelatin or the like may be used.

The composition of the present invention may be administered in a pharmaceutically effective amount.

As used herein, the phrase "pharmaceutically effective amount" refers to an amount sufficient to treat the disease at a reasonable benefit/risk ratio applicable to any medical treatment. An effective dose level may be determined depending on a variety of factors including the severity, age, and sex of the subject, the type of disease, activity, drug sensitivity, administration time, administration route, discharge ratio, treatment period, and co-administered drugs, and other factors well known in the medical field. The composition of the present invention may be administered alone or in combination with other therapeutics. The co-administration of the composition of the present invention with the conventional therapeutics may be carried out simultaneously or sequentially. Single or multiple dosages are possible. It is important Louse, the composition in the minimum possible amount sufficient to obtain the greatest therapeutic effect without side effects, considering all, the factors, and the amount can be readily determined by those skilled in the art. However, for preferable effects, the pharmaceutical composition of the present invention may be administered in an amount of 0.001 to 100 μg/kg per day, preferably 0.01 to 100 μg/kg per day via a parenteral or oral route. The dose may be administered in a single administration or divided into several times per day. The scope of the present invention is not to be limited to the dose in any aspect. The composition may be administered to various mammals, such as mouse, livestock or human, via various routes. All modes of administration are contemplated without limitation, as long as they are typical methods in the art, for example, administration can be made orally, rectally or by intravenous, intramuscular, subcutaneous, epidural or intracerebroventricular injection.

The composition for preventing or treating hangover of the present invention may further comprise an *Engelhardtia chrysolepis* HANCE extract, a *Nelumbo nucifera* seed extract, a *Hovenia dulcis* fruit extract or a mixture thereof as an auxiliary component for further improving the effect of hangover relief, in addition to the above main component. Preferably, it may further include vitamins such as vitamin B, vitamin C, vitamin E or beta-carotene, minerals such as Ca, Mg, or Zn, phospholipids such as lecithin, amino acids such as alanine or taurine, malic acid, citric acid, white sugar, high fructose corn syrup, oligosaccharide, *Ganoderma Lucidum*, or a mixture thereof.

In another aspect, the present invention provides a method for preventing or treating hangover, comprising the step of administering the composition to a subject having the symptoms of hangover or at the risk of having the symptoms of hangover.

Descriptions of the composition and hangover are the same as described above.

Specifically, the treatment method of the present invention includes administration of the composition in pharmaceutically effective amount to a subject having the symptoms of hangover or at the risk of having the symptoms of hangover. The subject means all mammals including dog, cow, horse, rabbit, mouse, rat, chicken, or human, but the mammal of the present invention is not limited to these examples. The composition may be administered via parenteral, subcutaneous, intraperitoneal, intrapulmonary and intranasal routes. For topical treatment, it may be administered by a suitable method including intralesional injection, if necessary. A preferred administration dose of the composition of the present invention may vary depending on the conditions and weight of a subject, severity of the illness, drug type, administration route and period, and may be readily determined by those skilled in the art.

In still another aspect, the present invention provides a food composition for preventing or relieving hangover including the *Laurus nobilis* leaf extract as an active ingredient.

The composition of the present invention may preferably further comprise an *Opuntia ficus* indica extract so as to be a composition comprising the *Laurus nobilis* leaf extract and the *Opuntia ficus* indica extract, and more preferably, further comprise a *Rosa roxburghii* extract so as to be a composition comprising the *Laurus nobilis* leaf extract, the *Opuntia ficus* indica extract, and the *Rosa roxburghii* extract. Most preferably, the composition may be a composition comprising the *Laurus nobilis* leaf extract, the *Opuntia ficus* indica extract, the *Rosa roxburghii* extract, an *Engelhardtia chrysolepis* HANCE extract, and a *Nelumbo nucifera* seed (Lotus) extract.

Descriptions of the *Laurus nobilis* leaf, *Opuntia ficus* indica, *Rosa roxburghii* extract and hangover are the same as described above.

Specifically, the extract of the present invention may be added to the food composition for the purpose of preventing or relieving hangover.

When the *Laurus nobilis* leaf extract of the present invention is used as a food additive, the extract or a fraction thereof may be added as it is, or used in combination with other foods or components, and properly used according to the typical method. The mixed amount of the active ingredients may be suitably determined depending on the purpose of use.

In addition, there is no specific limitation in the kinds of the food. Examples of the food to which the *Laurus nobilis* leaf extract can be added may include meat, sausages, bread, chocolates, candies, snacks, cookies, pizzas, instant noodles, other noodles, gums, jellies, and dairy products including ice-cream, a variety of soups, beverages, tea, drinks, alcoholic beverages, and vitamin complex. Actually, all kinds of food in general meaning may be included, and foods used as animal feed are also included.

In addition to the above, the food composition of the present invention may include various nutrients, vitamins, electrolytes, flavors, coloring agents, pectic acid and salts thereof, alginic acid and salts thereof, organic acid, a protective colloidal thickener, a pH regulator, a stabilizer, a preservative, glycerin, alcohol, carbonation agents for carbonated beverages, etc. Besides, the food composition may include flesh for producing natural fruit juice, fruit juice drink, and vegetable drink. Further, the food may be prepared into a formulation such as a tablet, a granule, a powder, a capsule, a liquid solution, a pill or the like according to the known preparation method. As long as the *Laurus nobilis* leaf extract of the present invention is included as an active ingredient, other ingredients are not particularly limited, and various flavors or natural carbohydrates typically used may be included as additive ingredients.

In still another aspect, the present invention provides a method for preparing the *Laurus nobilis* leaf extract; and the composition comprising the same.

Descriptions of the *Laurus nobilis* and *Laurus nobilis* leaf extract are the same as described above.

Specifically, the preparation method comprises the steps of (a) extracting a dry *Laurus nobilis* leaf sample with 1 to 100-fold (v/w) of water, alcohol having 1 to 6 carbon atoms or a mixed solvent thereof at 25° C. to 120° C. for 1 hour to 8 hours; and (b) preparing a *Laurus nobilis* leaf extract concentrate by filtering a extract produced in step (a) and concentrating it under reduced pressure.

Step (a) is a step of extracting from *Laurus nobilis* leaf leaves using an extraction solvent, that is, a step of extracting a *Laurus nobilis* leaf powder with water, alcohol having 1 to 6 carbon atoms, preferably, alcohol having 1 to 4 carbon atoms, or a mixed solvent thereof. The extraction may be preferably performed at 25° C. to 120° C. for 1 hr to 8 hours by cold immersion extraction, hot water extraction, ultrasonic extraction, reflux cold extraction, ultrahigh pressure extraction or heating extraction. However, as long as the method is used to prepare the extract showing the effect of preventing or relieving hangover, it is not particularly limited to the type thereof.

Step (b) is a step of preparing a *Laurus nobilis* leaf extract concentrate by filtering a extract produced in step (a) and concentrating it under reduced pressure.

The *Laurus nobilis* leaf extract; and the composition comprising the same may be prepared by the preparation method including the above steps.

Preferably, the method may further comprise the step of mixing an *Opuntia ficus* indica concentrated extract into the *Laurus nobilis* leaf concentrated extract of step (b), and more preferably, the step of mixing a *Rosa roxburghii* concentrated extract into a mixture of the *Laurus nobilis* leaf concentrated extract of step (b) and the *Opuntia ficus* indica concentrated extract.

MODE FOR INVENTION

Hereinafter, the constitution and effect of the present invention will be described in more detail with reference to Examples. However, these Examples are for illustrative purposes only, and the invention is not intended to be limited by these Examples

EXAMPLE 1

Preparation of *Laurus nobilis* Leaf Extract, *Opuntia ficus* Indica Extract and *Rosa roxburghii* Extract 1-1. Preparation of *Laurus nobilis* Leaf Extract 200 g of *Laurus nobilis* leaves were pulverized, and 2 L of hot water at 95° C. was added thereto, followed by extraction under stirring. The liquid extract was filtered through a filter paper, and then the supernatant was obtained and concentrated under reduced pressure to obtain a liquid concentrate. A *Laurus nobilis* leaf extract as a powder form was obtained by a spray-drying method.

1-2. Preparation of *Opuntia ficus* Indica Extract 200 g of *Opuntia ficus* indica fruits were pulverized, and 2 L of 80% ethanol at 80° C. was added thereto, followed by extraction under stirring for 6 hours. The liquid extract was filtered through a filter paper, and then the supernatant was obtained and concentrated under reduced pressure at a temperature of 50° C. to obtain a liquid concentrate with 50% solid content.

1-3. Preparation of *Rosa roxburghii* Extract

2 L of hot water at 95° C. was added to 200 g of *Rosa roxburghii* fruits, followed by extraction under stirring for 2 hours. The liquid extract was filtered through a filter paper, and then left for 12 hours. The supernatant was obtained and concentrated under reduced pressure to obtain a liquid concentrate with 50% solid content. Then, a *Rosa roxburghii* extract as a powder form was obtained by a spray-drying method.

EXAMPLE 2

Preparation of Composition for Preventing and Treating Hangover

An experimental composition including the *Laurus nobilis* leaf extract obtained in Example 1 was prepared. In detail, 50 mg of *Laurus nobilis* leaf extract, 100 mg of *Opuntia ficus* indica extract, 100 mg of *Rosa roxburghii* extract, 30 mg of *Engelhardtia chrysolepis* HANCE extract, 20 mg of *Nelumbo nucifera* seed (lotus) extract, 130 mg of *Hovenia dulcis* fruit extract concentrate, 340 mg of taurine, 34 mg of alanine, 9 mg of nicotinic acid amide, 34 mg of BCAA, 84 mg of vitamin C, 0.83 mg of vitamin B1 hydrochloride, 420 mg of white sugar, and 2,000 mg of high fructose corn syrup were added to 10 mL of distilled water to prepare the experimental composition.

Furthermore, a comparative composition including other components, except for the *Laurus nobilis* leaf extract and the *Opuntia ficus* indica extract, at the same weight ratio as in the experimental composition was prepared as a comparative group.

The experimental composition and comparative composition prepared as above were used to perform animal test in connection with hangover (Experimental Example 3).

EXAMPLE 3

Preparation of Drink for Preventing or Relieving Hangover

A drink for preventing or relieving hangover was prepared, based on Example 2. The administration dose for rats was converted into that for humans (60 kg/day for an adult) to prepare the drink. Specifically, based on 1 L (1000 g) of a mixture containing purified water, 3 g (0.3% by weight) of *Laurus nobilis* leaf extract, 6 g (0.6% by weight) of *Opuntia ficus* indica extract, 6 g (0.6% by weight) of *Rosa roxburghii* extract, 1.8 g (0.18% by weight) of *Engelhardtia chrysolepis* HANCE extract, 1.2 g (0.12% by weight) of *Nelumbo nucifera* seed (lotus) extract, 7.8 g (0.78% by weight) of *Hovenia dulcis* fruit extract concentrate, 20 g (2% by weight) of taurine, 1 g (0.1% by weight) of alanine, 0.53 g (0.053% by weight) of nicotinic acid amide, 2 g (0.2% by weight) of BCAA, 5 g (0.5% by weight) of vitamin C, 0.05 g (0.005% by weight) of vitamin B1 hydrochloride, 25 g (2.5% by weight) of white sugar, 120 g (12% by weight) of high fructose corn syrup, 1.6 g (0.16% by weight) of DL-malic acid, 3 g (0.3% by weight) of citric acid, 0.4 g (0.04% by weight) of sodium citrate, and 17 g (0.17% by weight) of flavors (mixed fruit flavor, honey flavor) were added, and water purified to be suitable for drinking was added thereto up to 1 L. The mixture was stirred until all of the components were completely dissolved and sterilized by a high-temperature-short-time (HTST) method to remove the remaining bacteria, and injected into a container. After injection into the container, post-process sterilization was performed to make the commodity temperature 80° C. or higher, and then the container was cooled, labeled, and packed to prepare a drink for hangover relief.

EXPERIMENTAL EXAMPLE 1

Investigation of Hangover-Preventing or Treating Effect of Different Doses of *Laurus nobilis* Leaf Extract In order to investigate the hangover-preventing or treating effect of single *Laurus nobilis* leaf extract, the experiment was performed at different doses (25 mg/kg, 50 mg/kg, and 100 mg/kg).

1-1. Measurement of Blood Concentrations of Alcohol and Acetaldehyde 7-week-old SD rats were stabilized for 1 week, and the *Laurus nobilis* leaf extract was administered to an experimental group at different doses of 25, 50, and 100 mg/kg, and then blood concentrations of alcohol and acetaldehyde were measured over time. In detail, fasted rats were divided into a control group (non-*Laurus nobilis* leaf extract-treated group; EtOH-treated group) and an experimental group (*Laurus nobilis* leaf extract-treated group). 25, 50, or 100 mg of *Laurus nobilis* leaf extract was dissolved in 1 ml and converted into the dose per body weight (B.W), and then orally administered to the rats of the experimental group. 30 minutes after administration, the control group and the experimental group were orally administered with 25% ethyl alcohol in an amount of 4 g/kg per body weight. After 1, 2, 4, and 8 hours from this baseline, 1.5 ml of blood was collected from the heart. Alcohol and acetaldehyde concentrations in the collected blood were analyzed by Headspace-GC/MS (Perkin Elmer, clarus 600T).

As shown in FIG. 1, a significant reduction in the blood concentrations of alcohol and acetaldehyde was observed in all experimental groups administered with 25, 50, or 100 mg of *Laurus nobilis* leaf extract, compared to the control group (non-*Laurus nobilis* leaf extract-treated group), indicating that the *Laurus nobilis* leaf extract has the effect of lowering blood concentrations of alcohol and acetaldehyde.

1-2. Behavioral Evaluation

In addition to the hematological test, behavioral evaluation on hangover symptoms due to alcohol, such as poor motor coordination, a decrease in motor functions, motor disturbance, sedation, muscle relaxation, and inability to control body temperature, was performed.

1-2-1. Measurement of Overall Motor Activity

A behavioral observation system and a program set such as EthoVision system (Noldus IT b.v., Netherlands) were used to examine movement distance, movement duration, movement angle, movement route or the like for a predetermined time while rats were placed in an open behavioral observation box and allowed to freely move around, which were utilized as basic data for evaluating all behaviors. This experiment was utilized for evaluating loss of motor functions, sedation, excitement, impulsive behavior or the like.

The day before the experiment, rats were adapted to the behavioral observation device once or more times for 10 minutes, and then 25, 50, or 100 mg of *Laurus nobilis* leaf extract was dissolved in 1 ml of distilled water and converted into the dose per body weight (B.W), and then orally administered to the rats of the experimental group, as in Experimental Example 1-1. 30 minutes after administration, the control group and the experimental group were orally administered with 25% ethyl alcohol in an amount of 4 g/kg per body weight. After 1, 2, 4, and 8 hours from this baseline, the rats were placed in the middle of the experimental box and stabilized for 2 minutes, followed by behavioral observation and analysis for 5 minutes. Total movement distance and total movement duration were evaluated.

Figure 2:
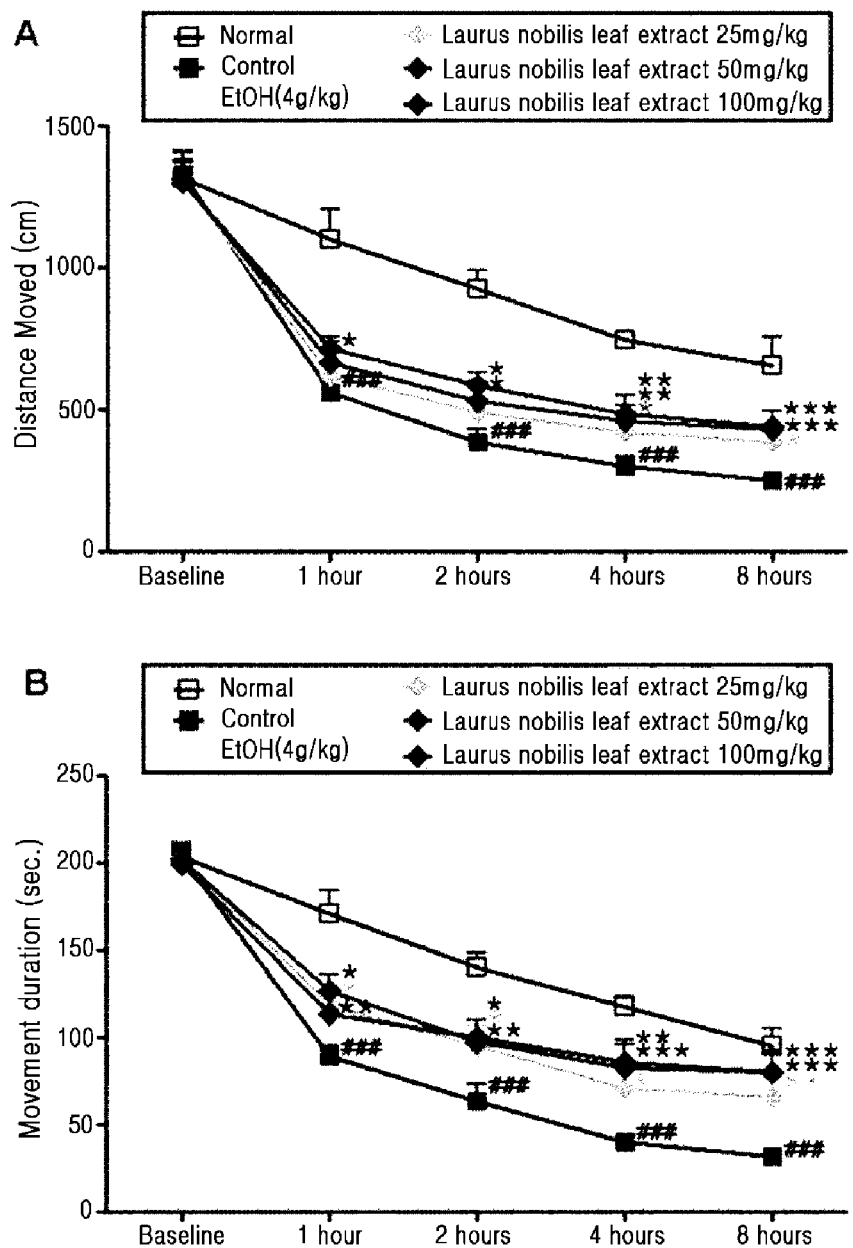
FIG. 2 is a graph showing overall motor activity, in which an alcohol-treated animal, after treatment of a control group (non-*Laurus nobilis* leaf extract-treated group; EtOH-treated group) and an experimental group (*Laurus nobilis* leaf extract-treated group), was placed in a behavioral observation box and (A) total movement distance and (B) total movement duration were evaluated (Mean±SEM, n=8/### p<0.001 versus Normal group/*p<0.05,  p<0.01 and * p<0.001 versus EtOH-treated group), Normal group represents a group of non-EtOH-treated normal rats.

As shown in FIG. 2, the overall motor activity was significantly reduced from 1 hour after alcohol administration. It was found that total movement distance (Distance Moved; cm) and total movement duration (Movement duration; sec.) of the experimental group (*Laurus nobilis* leaf extract-treated group) were significantly recovered, compared to the control group (non-*Laurus nobilis* leaf extract-treated group). Over time, the behaviors of the experimental group became close to those of the normal group which was not administered with *Laurus nobilis* leaf extract and ethyl alcohol, compared to the control group.

1-2-2. Measurement of Motor Activity on Rota-Rod

The experimental animal was placed on an RPM-adjustable treadwheel device, and the latency time to fall off, falling frequency, and mean latency time were measured and used for evaluating sedation, loss of motor functions, motor concentration, and an ability to maintain motion.

Animals were stabilized for 1 week, and they were trained for 5 minutes twice 2 days before the experiment and once one day before the experiment. 25, 50, or 100 mg of *Laurus nobilis* leaf extract was dissolved in 1 ml of distilled water and converted into the dose per body weight (B.W), and then orally administered to the rats of the experimental group, as in Experimental Example 1-1. 30 minutes after administration, the control group and the experimental group were orally administered with 25% ethyl alcohol in an amount of 4 g/kg per body weight. After 1, 2, 4, and 8 hours from this baseline, the rats were placed on the apparatus, and then mean latency time to fall (A) and falling frequency (B) were measured for 5 minutes. [Mean latency time=300 (s)/Falling frequency+1]

Figure 3:
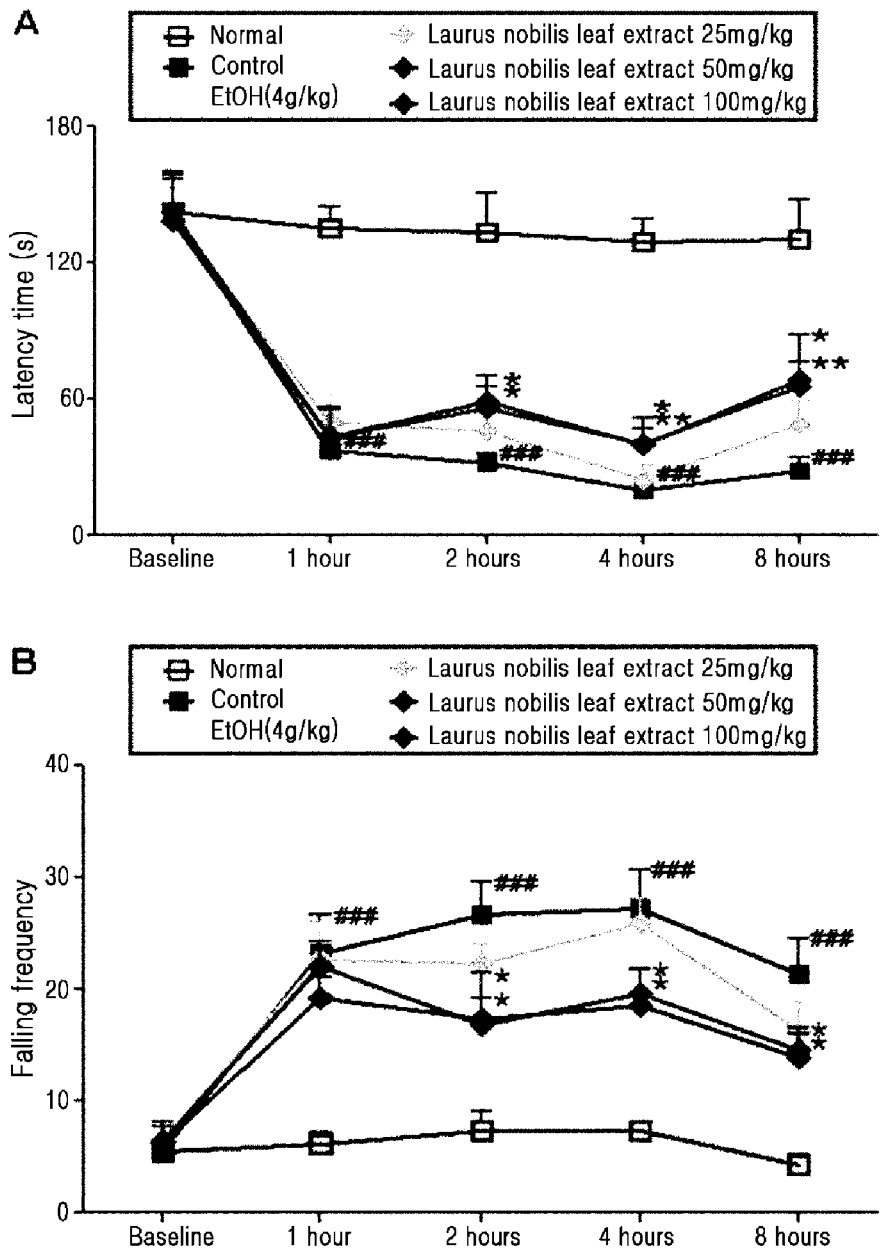
FIG. 3 is a graph showing motor activity on Rota-rod, in which an alcohol-treated animal after treatment of a control group (non-*Laurus nobilis* leaf extract-treated group; EtOH-treated group) and an experimental group (*Laurus nobilis* leaf extract-treated group) was placed on an apparatus and an RPM-adjustable treadwheel device was used to measure (A) latency time and (B) falling frequency for 5 minutes (Mean±SEM, n=8/### p<0.001 versus Normal group/*p<0.05,  p<0.01 and * p<0.001 versus EtOH-treated group)

As shown in FIG. 3, when alcohol was administered, the latency time was shortened and the falling frequency was increased. The experimental group showed an increase in the motor activity which had been reduced by alcohol administration, compared to the control group, and a significant difference in motor activity was observed from 2 hours after alcohol administration.

1-2-3. Measurement of Motor Activity on Wire

This test is to evaluate an ability of animals to cling to wires, and is a model used for evaluating loss of motor functions, an ability to maintain motion, motor concentration, sedation, muscle relaxation or the like. This data support the results of the above two experiments. This experiment was utilized for evaluating loss of motor functions, sedation, motor concentration or the like.

Animals were stabilized for 1 week, and they were trained in the apparatus twice for 2 days before the experiment (total 3 minutes; 1 minute for first time, 2 minutes for second time). 25, 50, or 100 mg of *Laurus nobilis* leaf extract was dissolved in 1 ml of distilled water and converted into the dose per body weight (B.W), and then orally administered to the rats of the experimental group, as in Experimental Example 1-1. 30 minutes after administration, the control group and the experimental group were orally administered with 25% ethyl alcohol in an amount of 4 g/kg per body weight. After 1, 2, 4, and 8 hours from this baseline, the rats were placed on the apparatus, and then mean latency time to fall (A) and falling frequency (B) were measured for 2 minutes. [Mean latency time=120 (s)/Falling frequency+1]

Figure 4:
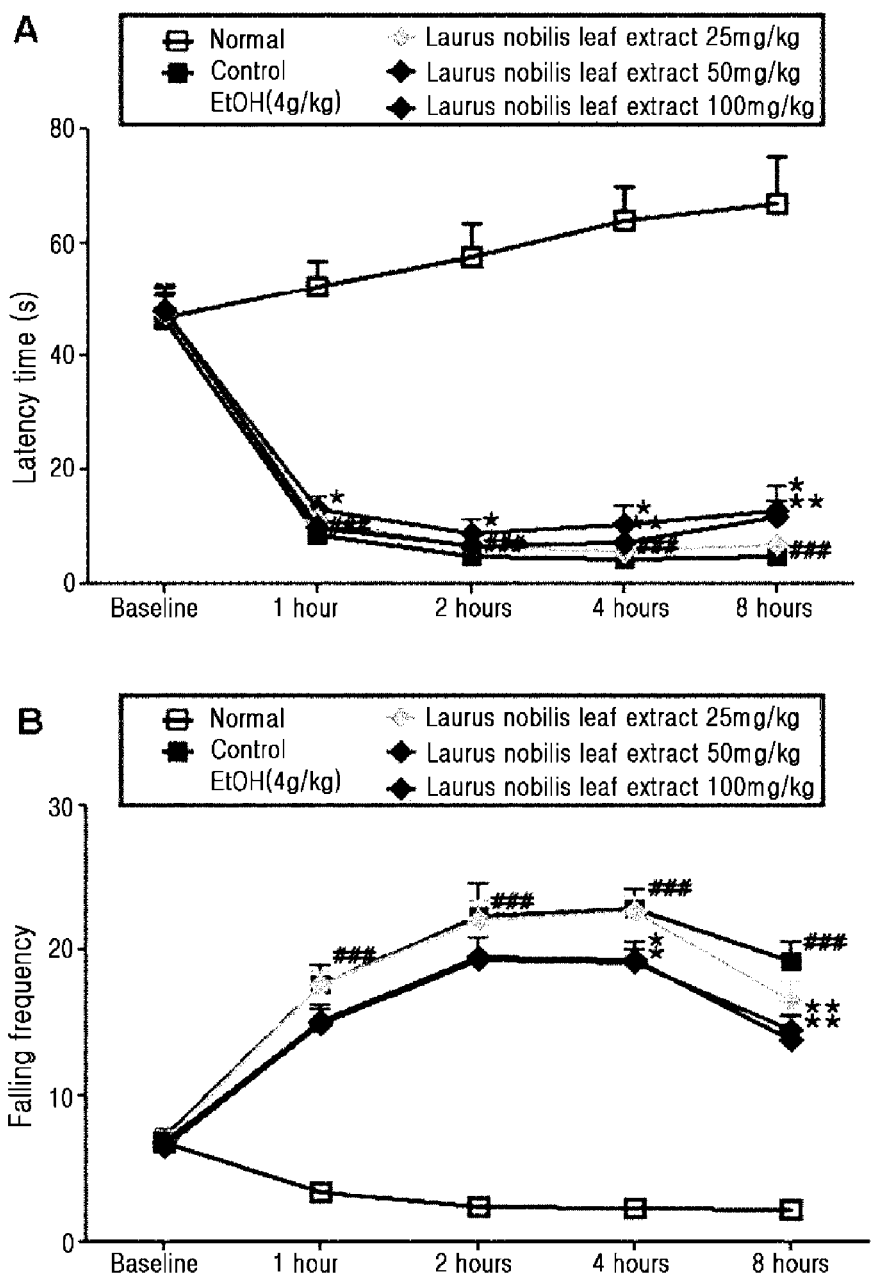
FIG. 4 is a graph showing motor activity on a wire, in which an alcohol-treated animal after treatment of a control group (non-*Laurus nobilis* leaf extract-treated group; EtOH-treated group) and an experimental group (*Laurus nobilis* leaf extract-treated group) was placed on an apparatus and (A) latency time and (B) falling frequency were measured for 2 minutes (Mean±SEM, n=8/### p<0.001 versus Normal group/*p<0.05,  p<0.01 and * p<0.001 versus EtOH-treated group)

As shown in FIG. 4, when alcohol was administered, the latency time was shortened and the falling frequency was increased. The experimental group showed an increase in the motor activity which had been reduced by alcohol administration, compared to the control group, and a significant difference in motor activity was observed from 4 hours after alcohol administration.

1-2-4. Cold Swimming Test

This test is to evaluate an ability of animal to endure cold water, and is a model used for evaluating resistance to stress, an ability to maintain motion, an ability to control body temperature, or the like.

An ability to maintain swimming in cold water (8±2° C.) is reduced due to reduction in the ability to control body temperature upon hangover. 25, 50, or 100 mg of *Laurus nobilis* leaf extract was dissolved in 1 ml of distilled water and converted into the dose per body weight (B.W), and then orally administered to the rats of the experimental group, as in Experimental Example 1-1. 30 minutes after administration, the control group and the experimental group were orally administered with 25% ethyl alcohol in an amount of 4 g/kg per body weight. After 1, 2, 4, and 8 hours from this baseline, the rats were allowed to swim in a cold pool and the latency time to give up swimming (up to 10 minutes) was measured.

Figure 5:
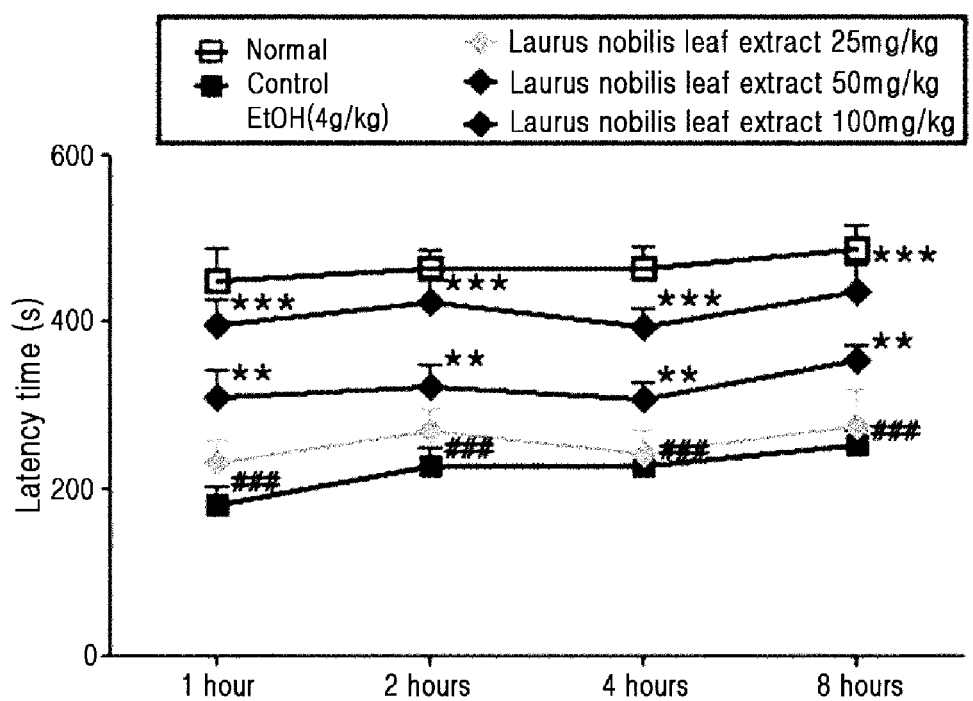
FIG. 5 is a graph showing cold swimming ability, in which an alcohol-treated animal after treatment of a control group (non-*Laurus nobilis* leaf extract-treated group; EtOH-treated group) and an experimental group (*Laurus nobilis* leaf extract-treated group) was allowed to swim in a cold pool and the latency time before giving up swimming was measured (Mean±SEM, n=10/* p<0.05 versus EtOH-treated group)

As shown in FIG. 5, when alcohol was administered, the ability to control body temperature and the motor activity were reduced, and thus cold swimming ability was significantly reduced. The experimental group showed significant recovery in the cold swimming ability in a dose-dependent manner, compared to the control group.

EXPERIMENTAL EXAMPLE 2

Investigation of Hangover-Preventing or Treating Effect of a Composition Comprising *Laurus nobilis* Leaf Extract with an Optimal Composition Ratio This experiment was performed to investigate the optimal composition ratio of a mixed composition of *Laurus nobilis* leaf extract, *Opuntia ficus* indica extract and *Rosa roxburghii* extract. The dose of the *Laurus nobilis* leaf extract was determined based on the result of Experimental Example 1 as follows, and then the experiment was performed. Composition A was prepared using 100 mg of *Laurus nobilis* leaf extract, 100 mg of *Opuntia ficus* indica extract, and 100 mg of *Rosa roxburghii* extract, Composition B was prepared using 100 mg of *Laurus nobilis* leaf extract, 100 mg of *Opuntia ficus* indica extract, and 50 mg of *Rosa roxburghii* extract, Composition C was prepared using 50 mg of *Laurus nobilis* leaf extract, 100 mg of *Opuntia ficus* indica extract, and 100 mg of *Rosa roxburghii* extract, and Composition D was prepared using 100 mg of *Laurus nobilis* leaf extract, 200 mg of *Opuntia ficus* indica extract, and 100 mg of *Rosa roxburghii* extract. They are summarized in the following Table 1.

TABLE 1

Composition ratio of mixed extract composition

| | Experimental group A | Experimental group B | Experimental group C | Experimental group D |
|---|---|---|---|---|
| *Laurus nobilis* leaf extract (mg) | 100 | 100 | 50 | 100 |
| *Opuntia ficus indica* extract (mg) | 100 | 100 | 100 | 200 |
| *Rosa roxburghii* extract (mg) | 100 | 50 | 100 | 100 |

2-1. Measurement of Blood Concentration of Alcohol 7-week-old SD rats were stabilized for 1 week, and the stabilized rats were divided into a control group (non-composition-treated group; EtOH-treated group) and an experimental group (composition-treated group). The rats of the experimental group were administered with A to D, and alcohol blood concentrations of the rats of the control group and the experimental group were measured over time. In detail, rats were divided into A, B, C, D, and Compositions A, B, C, D were dissolved in 1 ml of distilled water and converted into the dose per body weight (B.W), and then orally administered to the rats, as in Experimental Example 1-1. 30 minutes after administration, the rats were orally administered with ethyl alcohol. After 30 minutes, 1, 2, 4, and 8 hours from this baseline, blood was collected. Alcohol concentrations were analyzed.

Figure 6:
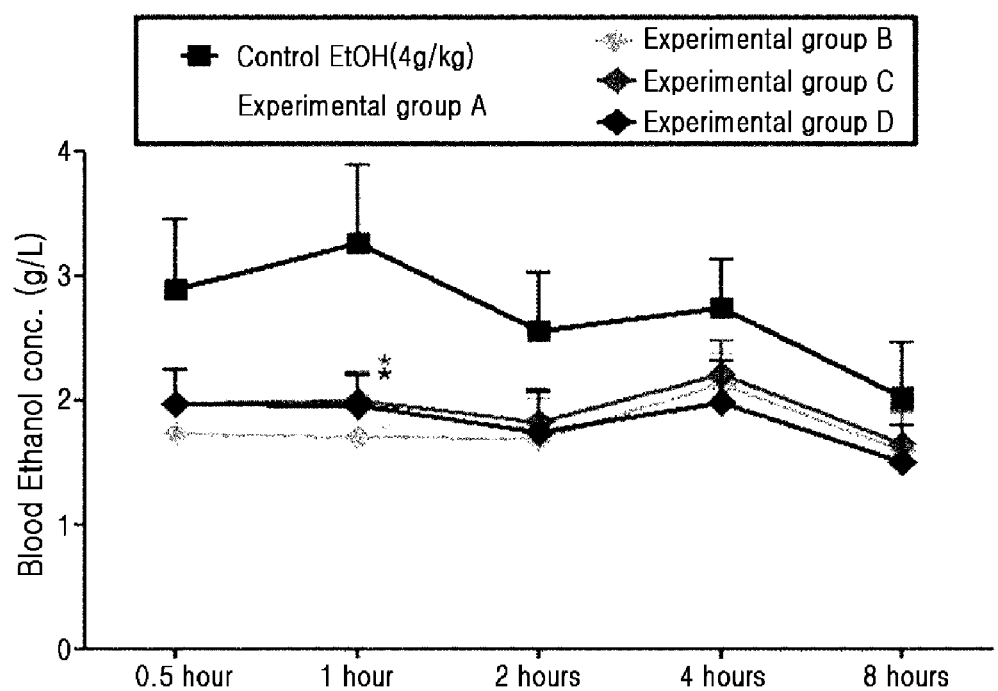
FIG. 6 is a graph showing blood alcohol concentration of the alcohol-treated animals after treatment of a control group (non-composition-treated group; EtOH-treated group) and an experimental group (composition-treated group) (Mean±SEM, n=10/# p<0.05, ### p<0.001 versus Normal group/*p<0.05 and ** p<0.001 versus EtOH-treated group)

As shown in FIG. 6, low alcohol blood concentrations were observed to become lower in all experimental groups compared to the control group, from 30 minutes after alcohol administration, and a significant difference was observed at 1 hour after alcohol administration.

2-2. Behavioral Evaluation

In addition to the hematological test, behavioral evaluation on hangover symptoms due to alcohol, such as poor motor coordination, a decrease in motor functions, motor disturbance, sedation, muscle relaxation, and inability to control body temperature, was performed.

2-2-1. Measurement of Overall Motor Activity

The day before the experiment, rats were adapted to the behavioral observation device once or more times for 10 minutes in the same manner as in Experimental Example 1-2-1, and rats were divided into experimental groups, A, B, C, D, and Compositions A, B, C, D were dissolved in 1 ml of distilled water and converted into the dose per body weight (B.W), and then orally administered to the rats, in the same manner as in Experimental Example 2-1. 30 minutes after administration, the rats were orally administered with ethyl alcohol. After 30 minutes, 1, 2, 4, and 8 hours from this baseline, the rats were placed in the middle of the experimental box and stabilized for 2 minutes, followed by behavioral observation for 5 minutes and analysis thereof. Total movement distance and total movement duration were evaluated.

Figure 7:
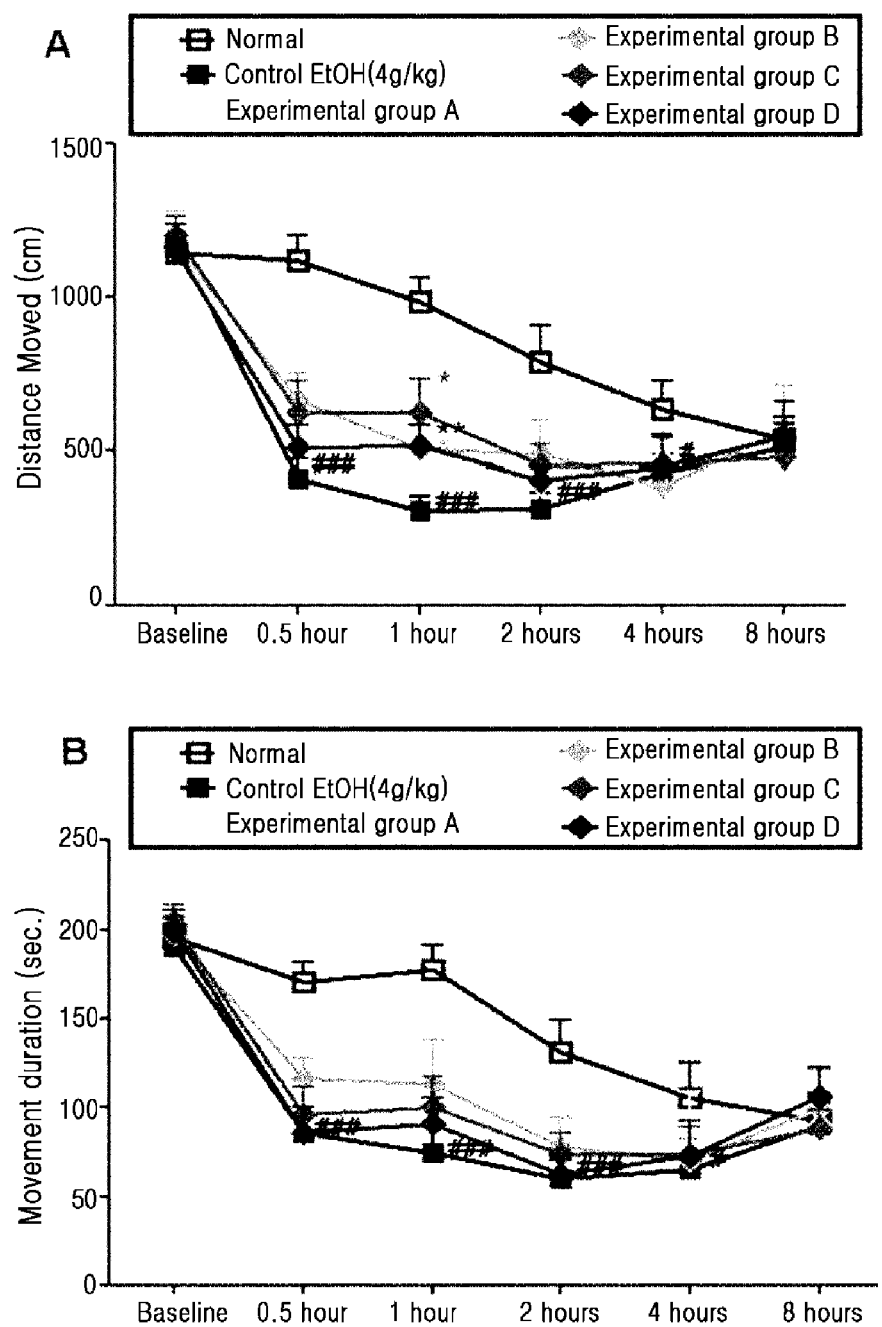
FIG. 7 is a graph showing overall motor activity, in which an alcohol-treated animal after treatment of a control group (non-composition-treated group; EtOH-treated group) and an experimental group (composition-treated group) was placed in a behavioral observation box and (A) total movement distance and (B) total movement duration were evaluated (Mean±SEM, n=10/# p<0.05, ### p<0.001 versus Normal group/*p<0.05 and ** p<0.01 versus EtOH-treated group)
Figure 8A:
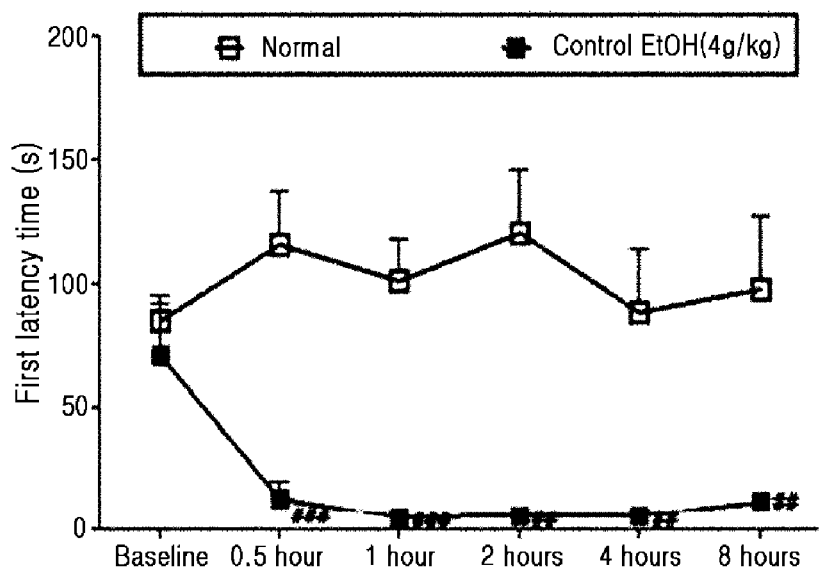
FIG. 8 is a graph showing motor activity on Rota-rod, in which an alcohol-treated animal after treatment of a control group (non-composition-treated group; EtOH-treated group) and an experimental group (composition-treated group) was placed on an apparatus and an RPM-adjustable treadwheel device was used to measure (A) first latency time, (B) falling frequency, and (C) mean latency time for 5 minutes (Mean±SEM, n=10/## p<0.01, ### p<0.001 versus Normal group/*p<0.05, ** p<0.01 versus EtOH-treated group)
Figure 8A:
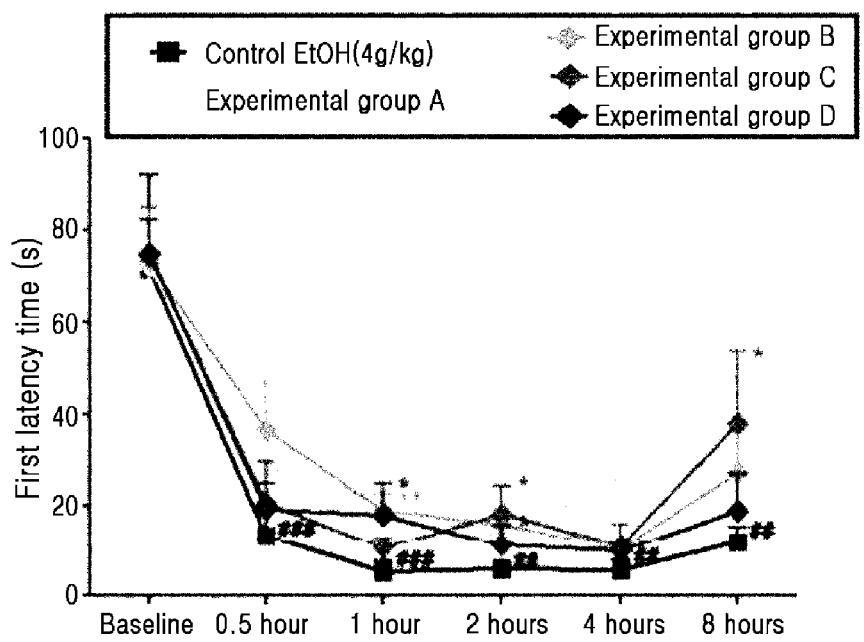
Figure 8B:
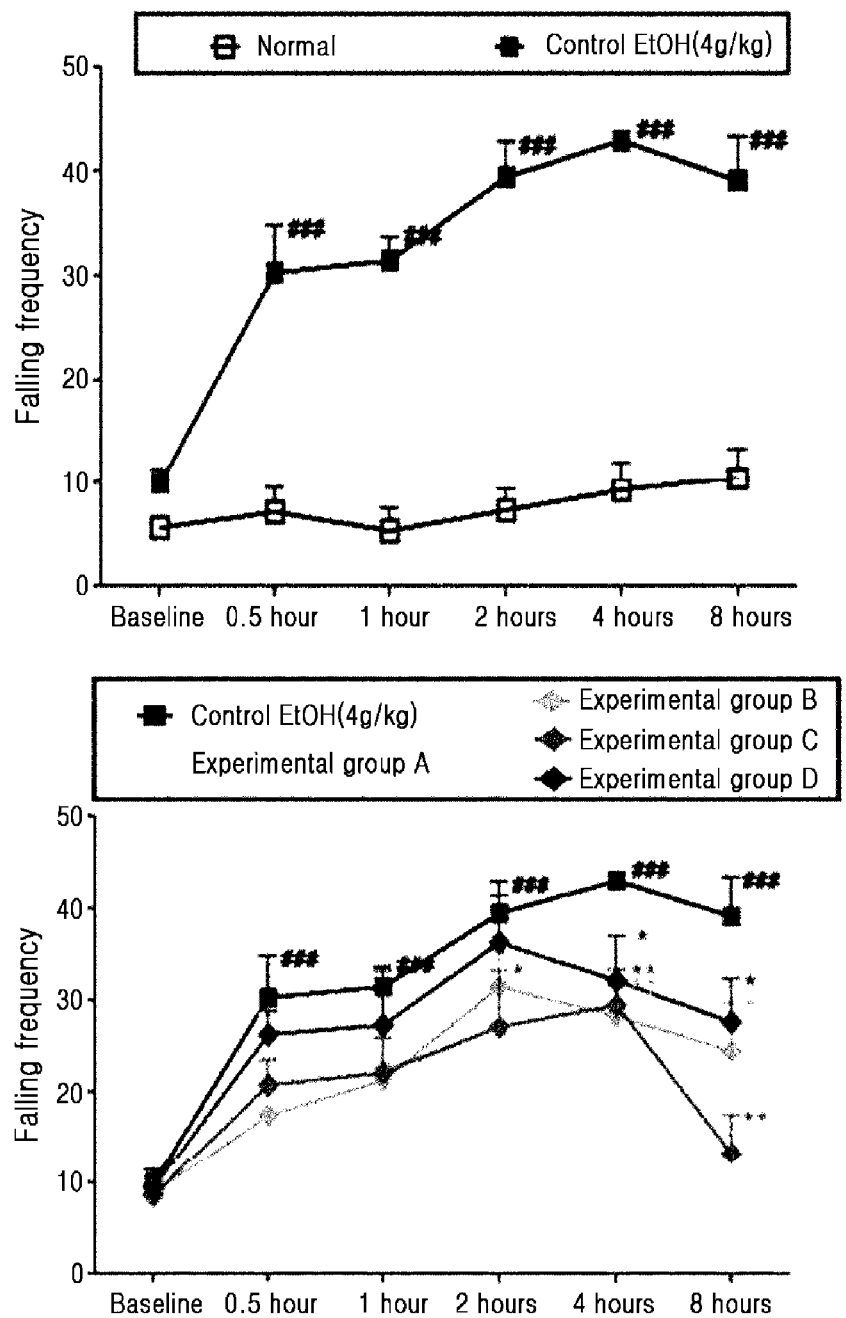
Figure 8C:
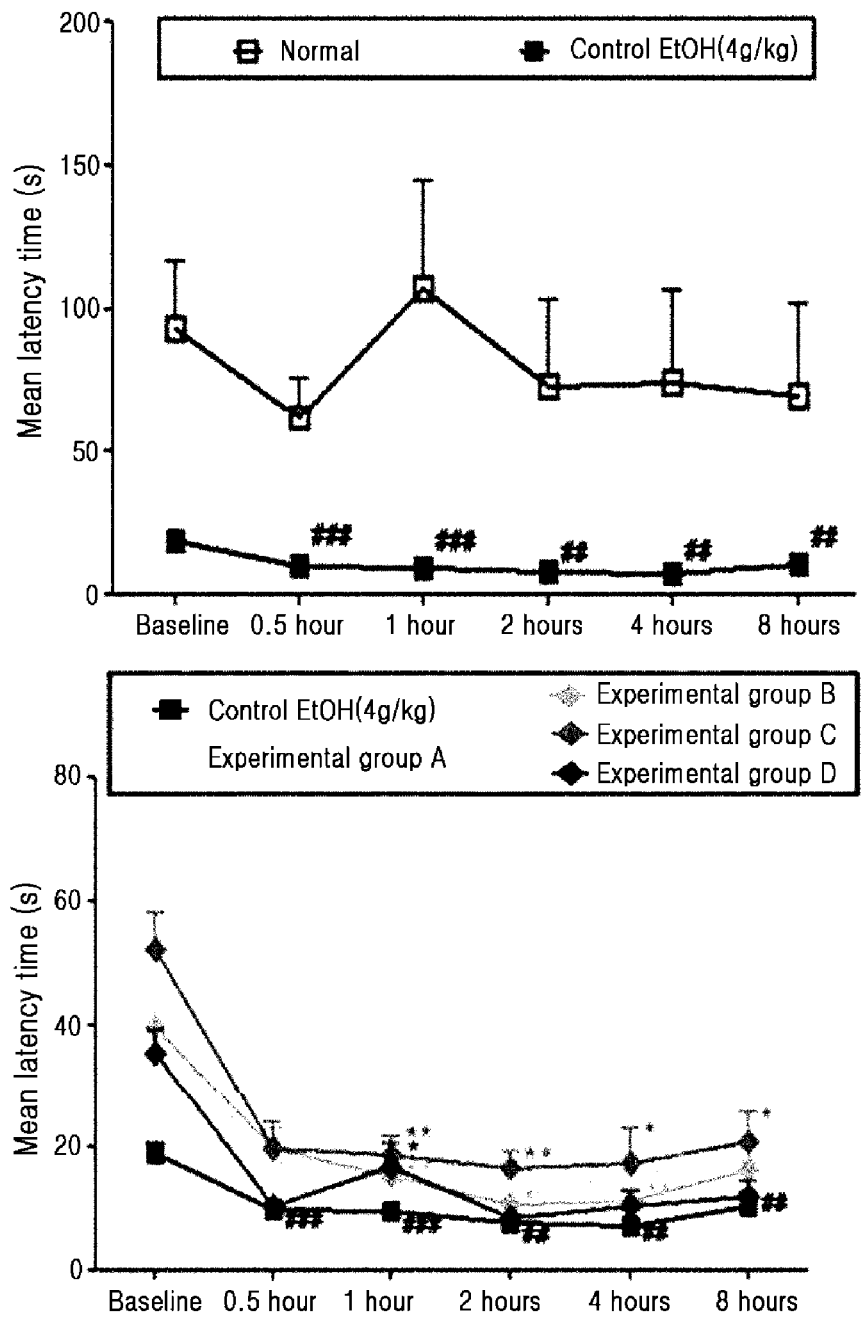
Figure 9A:
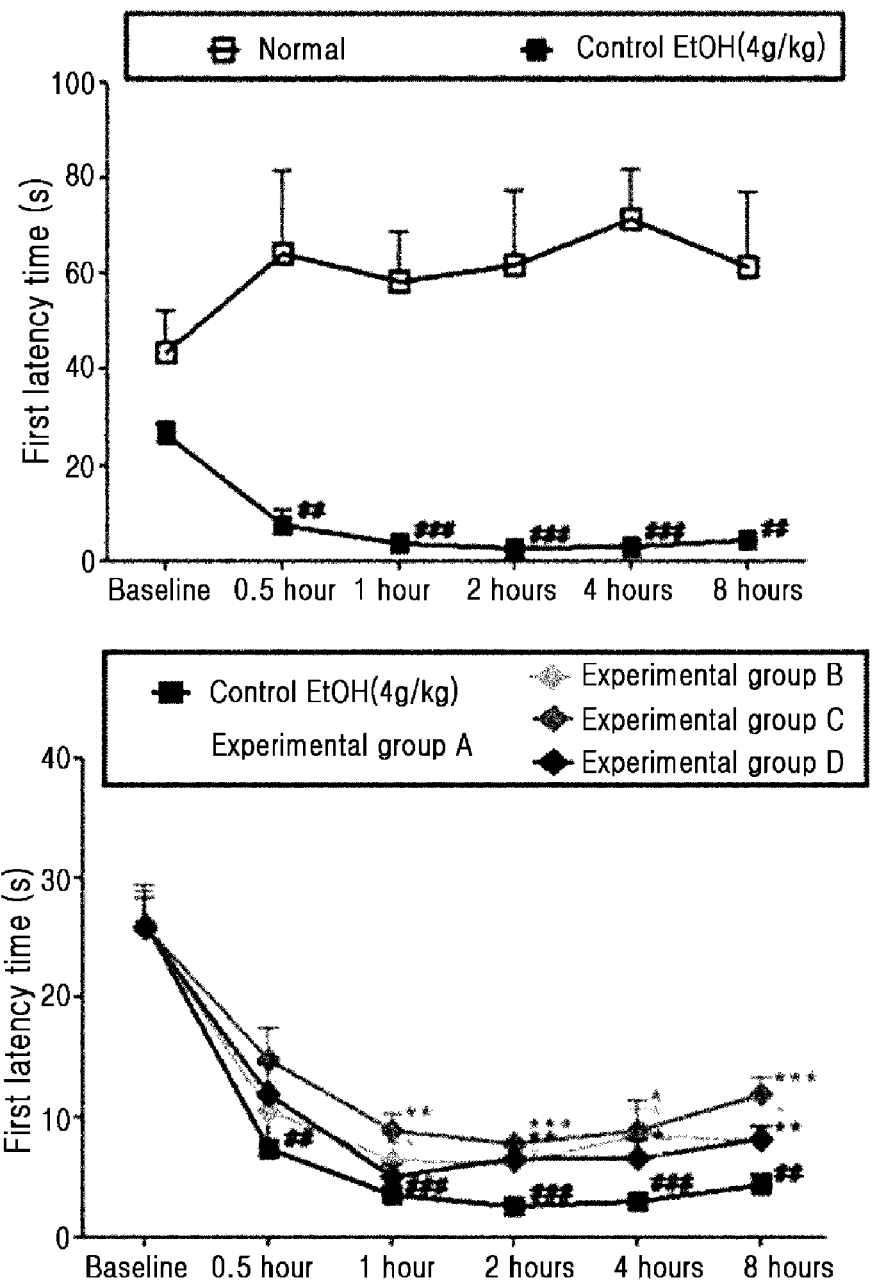
FIG. 9 is a graph showing motor activity on a wire, in which an alcohol-treated animal after treatment of a control group (non-composition-treated group; EtOH-treated group) and an experimental group (composition-treated group) was placed on an apparatus and (A) first latency time, (B) falling frequency, and (C) mean latency time were measured for 2 minutes (Mean±SEM, n=10/## p<0.01, ### p<0.001 versus Normal group/*p<0.05,  p<0.01 and * p<0.001 versus EtOH-treated group.
Figure 9B:
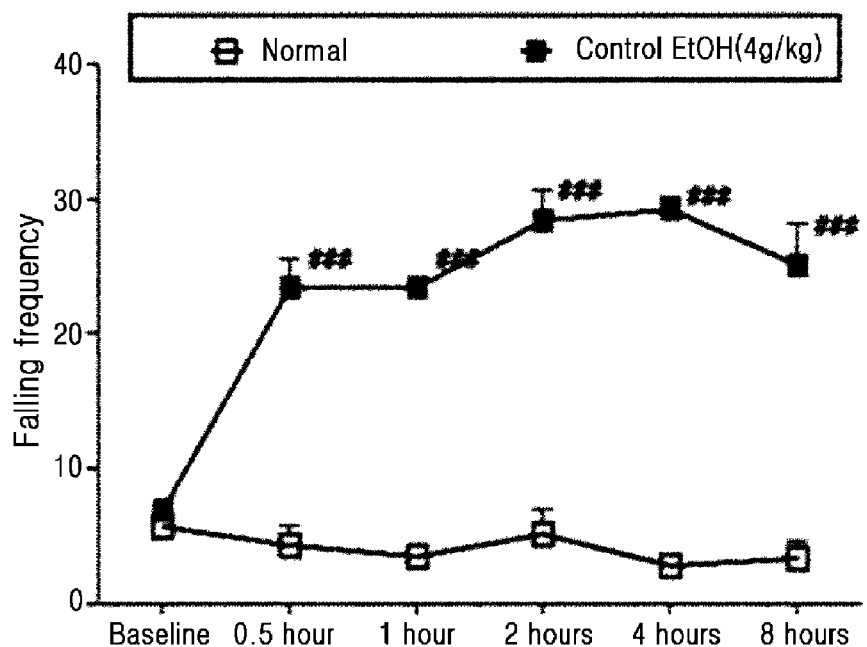
Figure 9B:
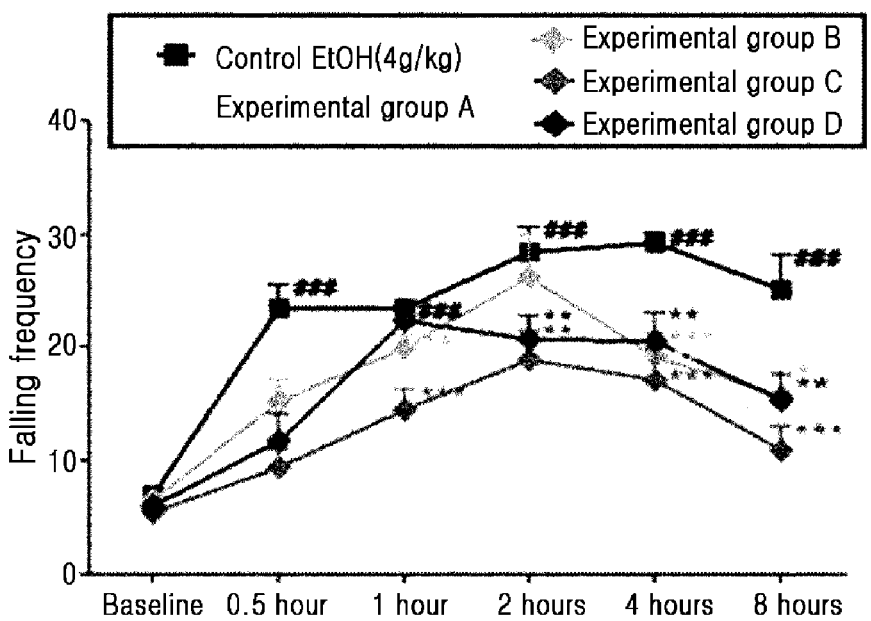
Figure 9C:
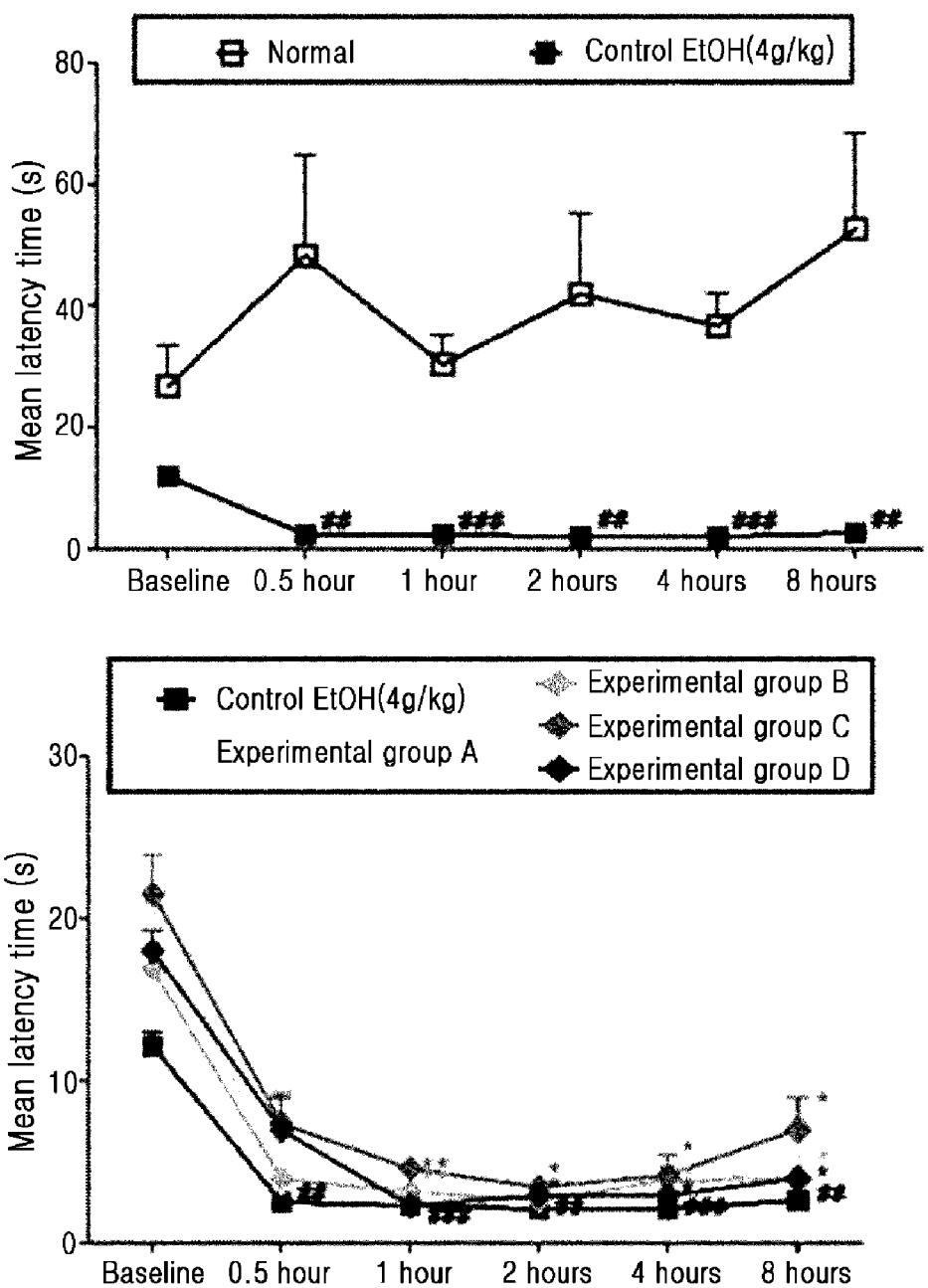

As shown in FIG. 7, the overall motor activity started to be significantly reduced from 30 minutes after alcohol administration. It was found that total movement distance and total movement duration of all the experimental groups were significantly increased, compared to those of the control group.

2-2-2. Measurement of Motor Activity on Rota-Rod

Animals were stabilized for 1 week, and they were trained for 5 minutes twice 2 days before the experiment and once one day before the experiment in the same manner as in Experimental Example 1-2-2. The rats were divided into Experimental groups A, B, C, D, and Compositions A, B, C, D were dissolved in 1 ml of distilled water and converted into the dose per body weight (B.W), and then orally administered to the rats, in the same manner as in Experimental Example 2-1. 30 minutes after administration, the rats were orally administered with ethyl alcohol. After 30 minutes, 1, 2, 4, and 8 hours from this baseline, the rats were placed on the apparatus, and then mean latency time to fall (A), falling frequency (B) and mean latency time (C) were measured for 5 minutes. [Mean latency time=300 (s)/Falling frequency+1]

As shown in FIG. 8, when alcohol was administered, the latency time was rapidly shortened and the falling frequency was rapidly increased. All the experimental groups showed an increase in the motor activity which had been reduced by alcohol administration, compared to the control group, and a significant difference in motor activity was observed from 1 hour after alcohol administration.

2-2-3. Measurement of Motor Activity on Wire

Animals were stabilized for 1 week, and they were trained in the apparatus twice for 2 days before the experiment (total 3 minutes; 1 minute for first time, 2 minutes for second time) in the same manner as in Experimental Example 1-2-3, and rats were divided into Experimental groups A, B, C, D, and Compositions A, B, C, D were dissolved in 1 ml of distilled water and converted into the dose per body weight (B.W), and then orally administered to the rats, in the same manner as in Experimental Example 2-1. 30 minutes after administration, the rats were orally administered with ethyl alcohol. After 30 minutes, 1, 2, 4, and 8 hours from this baseline, the rats were placed on the apparatus, and then mean latency time to fall (A), falling frequency (B) and mean latency time (C) were measured for 2 minutes.

As shown in FIG. 9, when alcohol was administered, the latency time was shortened and the falling frequency was increased. All the experimental groups showed significant recovery in the motor activity, compared to the control group. In addition, Experimental group C administered with Composition C showed the most excellent effect of recovering the motor activity which had been reduced by alcohol administration.

2-2-4. Cold Swimming Test

Rats were divided into Experimental groups A, B, C, D, and Compositions A, B, C, D were dissolved in 1 ml of distilled water and converted into the dose per body weight (B.W), and then orally administered to the rats, in the same manner as in Experimental Example 1-2-4. 30 minutes after administration, the rats were orally administered with ethyl alcohol. After 30 minutes, 1, 2, 4, and 8 hours from this baseline, the rats were allowed to swim in a cold pool and the latency time to give up swimming (up to 10 minutes) was measured.

Figure 10:
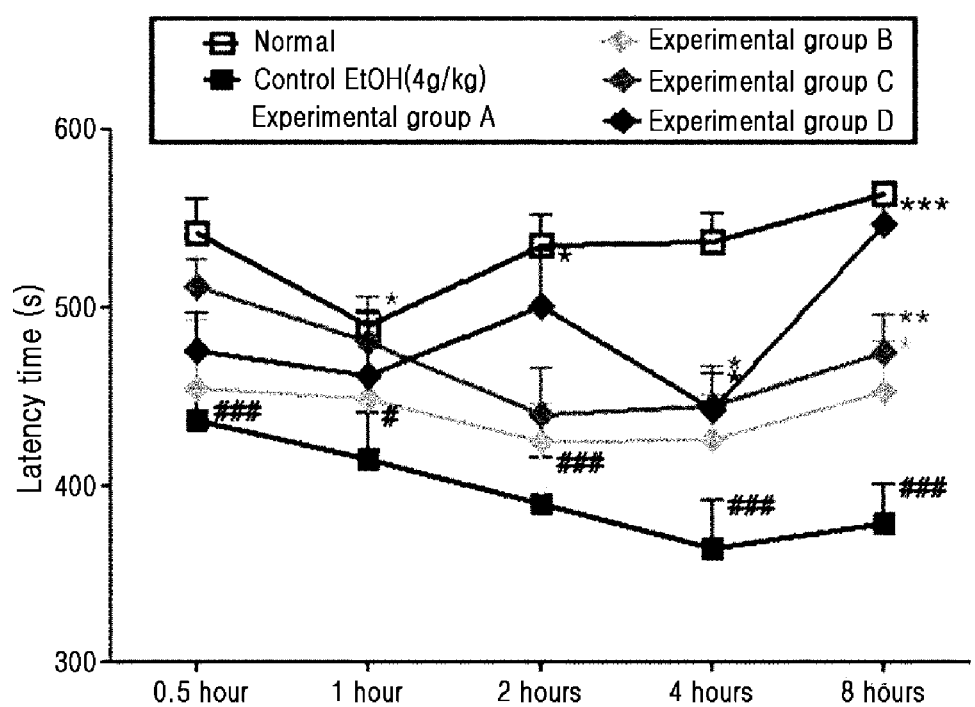
FIG. 10 is a graph showing cold swimming ability, in which an alcohol-treated animal after treatment of a control group (non-composition-treated group; EtOH-treated group) and an experimental group (composition-treated group) was allowed to swim in a cold pool and the latency time before giving up swimming was measured (Mean±SEM, n=10/# p<0.05, ### p<0.001 versus Normal group/* p<0.05,  p<0.01 and * p<0.001 versus EtOH-treated group)

As shown in FIG. 10, when alcohol was administered, the ability to control body temperature and the motor activity were reduced, and thus cold swimming ability was significantly reduced. All the experimental groups showed significant recovery in the cold swimming ability, compared to the control group.

As the overall results of examining the effects of increasing alcohol metabolism to reduce blood alcohol concentration and improving the motor activity and the ability to control body temperature that were reduced by alcohol administration, Experimental group C (*Laurus nobilis* leaf extract *Opuntia ficus* indica extract:*Rosa roxburghii* extract=50 mg/kg:100 mg/kg:100 mg/kg) has been confirmed that it has the most effective composition ratio of *Laurus nobilis* leaf extract, *Opuntia ficus* indica extract and *Rosa roxburghii* extract thereby exhibiting the best effect in hangover-relief.

EXPERIMENTAL EXAMPLE 3

Investigation of Hangover-Preventing or Treating Effect of Composition for Preventing and Treating Hangover Based on the optimal composition ratio of *Laurus nobilis* leaf extract, *Opuntia ficus* indica extract and *Rosa roxburghii* extract (Experimental Example 2), compositions (Example 2; experimental composition and comparative composition) containing other materials were prepared and the experiment was performed. Moreover, the effects of the corresponding composition on behaviors according to administration dose were demonstrated.

3-1. Measurement of Blood Concentrations of Alcohol and Acetaldehyde 7-week-old SD rats were stabilized for 1 week, and the stabilized rats were divided into an experimental group, a comparative group and a control group. The experimental composition and comparative composition prepared in Example 2 were dissolved in 10 mL of distilled water for convenience and converted into the dose per body weight (B.W), and 10-fold (high dose (100%) administration) and 5-fold (low dose (50%) administration) administrations were performed. The rats of the experimental group and the comparative group were administered with the dose per body weight, and blood concentrations of alcohol and acetaldehyde were measured over time. In detail, the experiment was performed in the same manner as in Experimental Example 1-1.

Figure 11A:
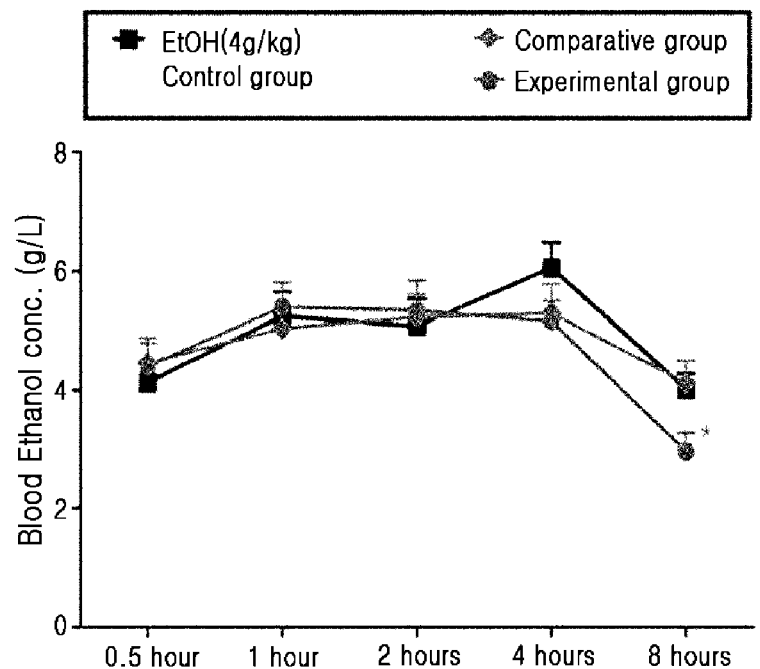
FIG. 11 is a graph showing (A) blood alcohol concentration and (B) blood acetaldehyde concentration of the alcohol-treated animals after treatment of a control group (non-composition-treated group; EtOH-treated group), an experimental group (experimental composition-treated group) and a comparative group (comparative composition-treated group) (Mean±SEM, n=10. *p<0.05)
Figure 11A:
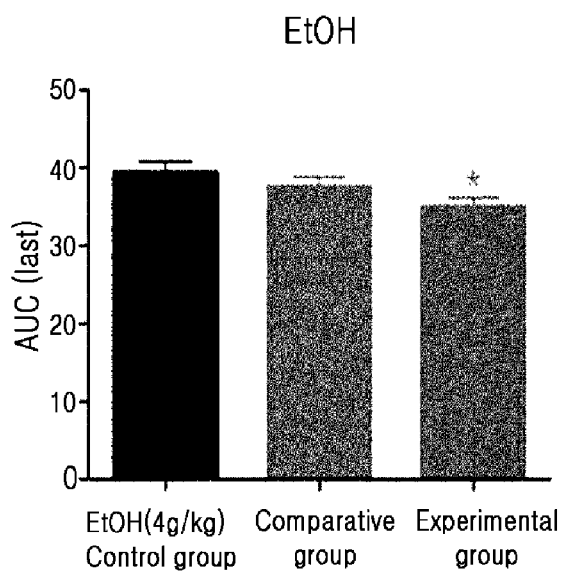
Figure 11B:
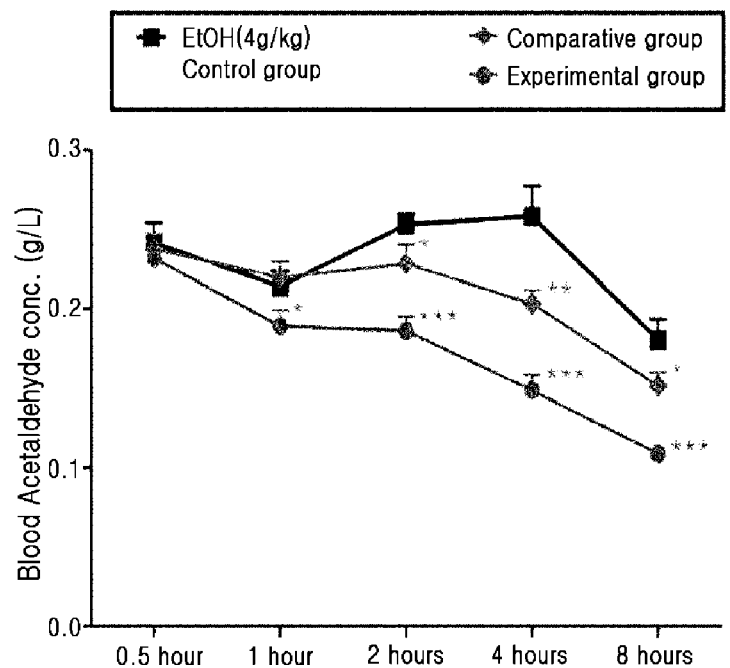
Figure 11B:
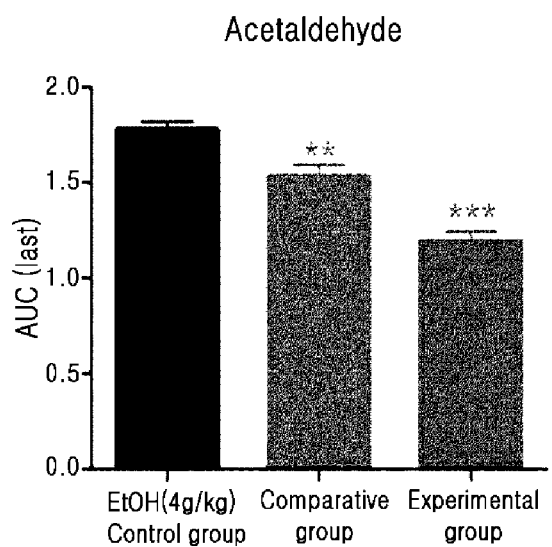

As shown in FIG. 11, at 4 hours after oral administration of alcohol, blood concentrations of alcohol were remarkably reduced in the experimental group (experimental composition-treated group) and comparative group (comparative composition-treated group), compared to the control group (non-experimental composition-treated group), and at 8 hours after oral administration, the comparative group and the control group showed similar blood concentrations of alcohol, but the experimental group of the present invention showed a remarkably low blood concentration of alcohol (FIG. 11(A)). Moreover, the blood concentration of acetaldehyde which is a direct cause of hangover was remarkably reduced in the experimental group from 1 hour after oral administration of alcohol, compared to the control group and the comparative group (FIG. 11(B)). In addition, the comparison of the area under curve (AUC) of blood concentration for alcohol and acetaldehyde showed that blood concentrations of both alcohol and acetaldehyde were statistically significant low in the experimental group, compared to the control group.

3-2. Behavioral Evaluation

In addition to the hematological test, behavioral evaluation on hangover symptoms due to alcohol, such as poor motor coordination, a decrease in motor functions, motor disturbance, sedation, muscle relaxation, and inability to control body temperature, was performed. In particular, low dose (50%) and high dose (100%)-administered groups were compared by varying the administration dose of the composition of the present invention, and it was examined whether the composition of the present invention has a dose-dependent effect.

3-2-1. Measurement of Overall Motor Activity

The day before the experiment, rats were adapted to the behavioral observation device once or more times for 10 minutes in the same manner as in Experimental Example 1-2-1, and the experimental composition and the comparative composition prepared in Example 2 were administered to rats of low dose (50%) and high dose (100%) experimental groups and comparative group, respectively. The rats were divided into Experimental groups A, B, C, D, and Compositions A, B, C, D were orally administered to the rats. 30 minutes after administration, the rats were orally administered with ethyl alcohol. After 30 minutes, 1, 2, 4, and 8 hours from this baseline, the rats were placed in the middle of the experimental box and stabilized for 2 minutes, followed by behavioral observation for 5 minutes and analysis. Total movement distance and total movement duration were evaluated.

Figure 12:
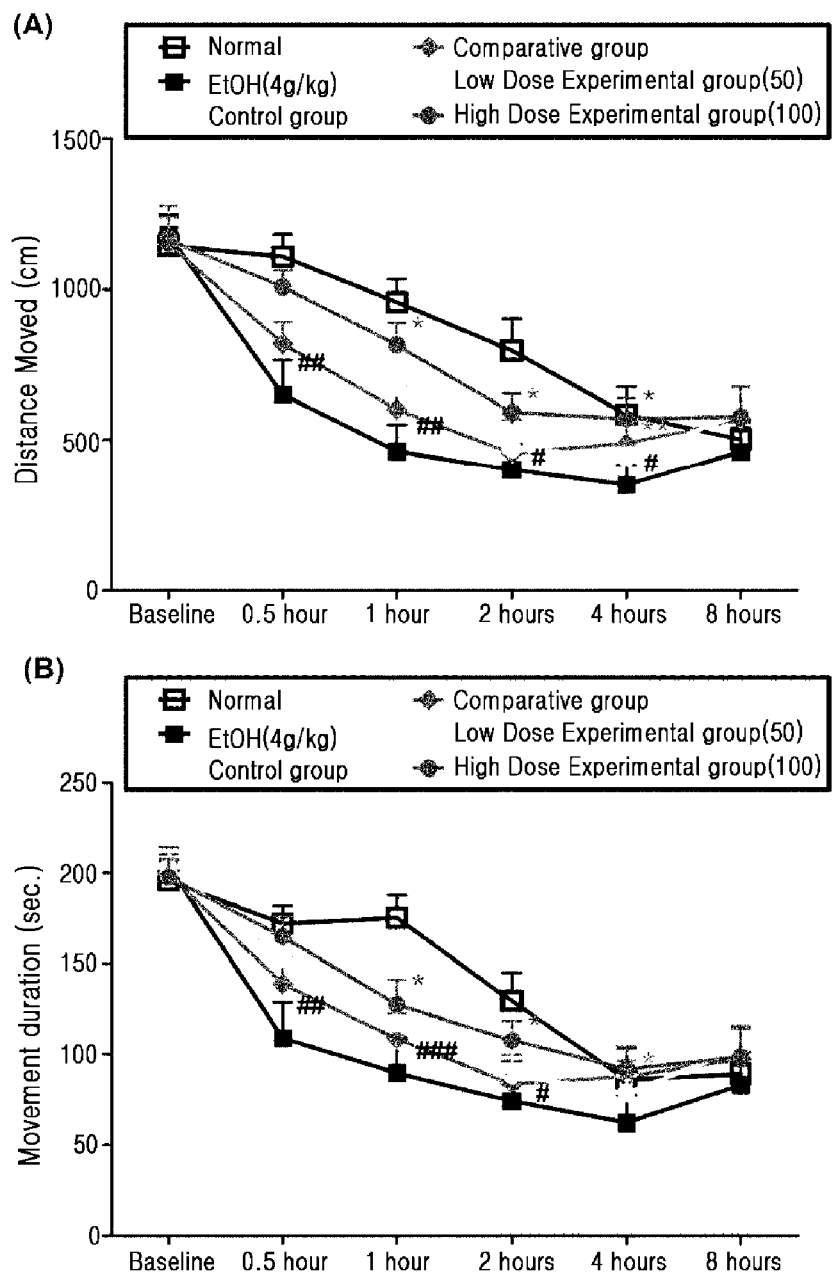
FIG. 12 is a graph showing overall motor activity, in which an alcohol-treated animal after treatment of a control group (non-composition-treated group; EtOH-treated group), low dose (50%) and high dose (100%) experimental groups (experimental composition-treated group) and a comparative group (comparative composition-treated group) was placed in a behavioral observation box and (A) total movement distance and (B) total movement duration were evaluated (Mean±SEM, n=10/# p<0.05, ## p<0.01 and ### p<0.001 versus Normal group/*p<0.05 and ** p<0.01 versus EtOH-treated group)
Figure 13A:
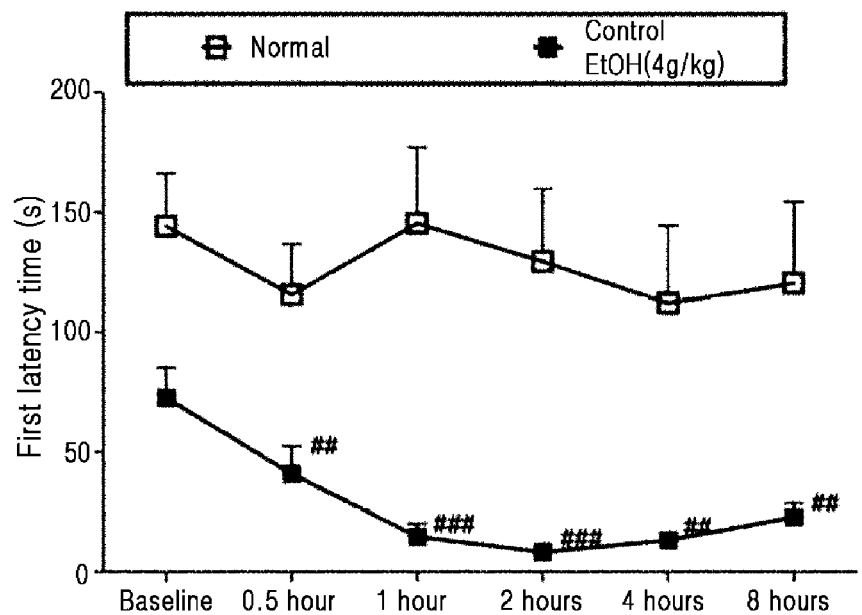
FIG. 13 is a graph showing motor activity on Rota-rod, in which an alcohol-treated animal after treatment of a control group (non-composition-treated group; EtOH-treated group), low dose (50%) and high dose (100%) experimental groups (experimental composition-treated group) and a comparative group (comparative composition-treated group) was placed on an apparatus and an RPM-adjustable treadwheel device was used to measure (A) first latency time, (B) falling frequency, and (C) mean latency time (Mean±SEM, n=10/## p<0.01 and ### p<0.001 versus Normal group/*p<0.05,  p<0.01 and * p<0.001 versus EtOH-treated group)
Figure 13A:
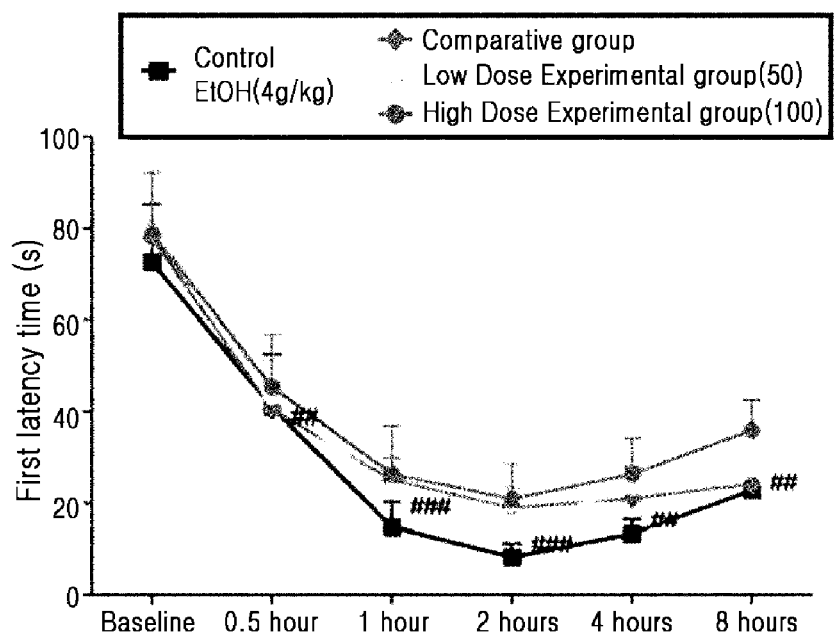
Figure 13B:
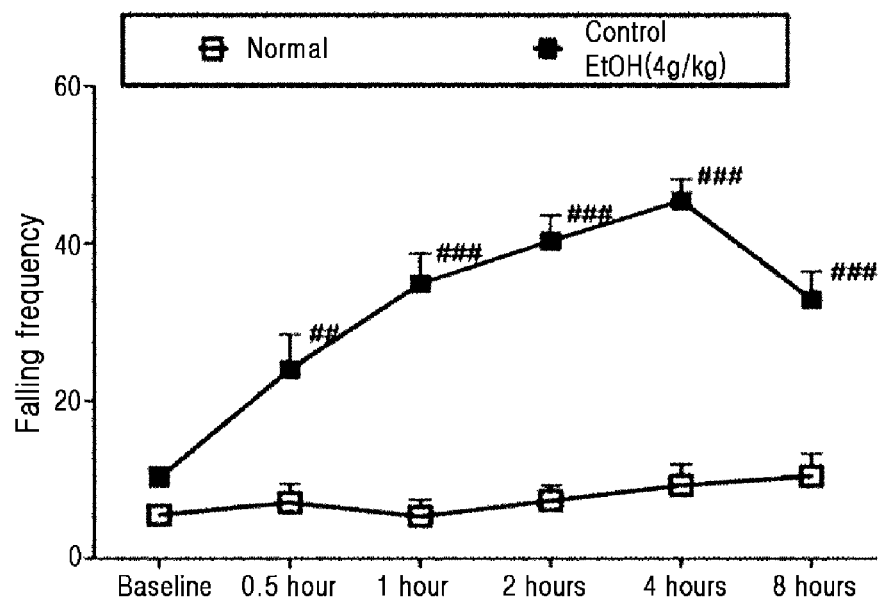
Figure 13B:
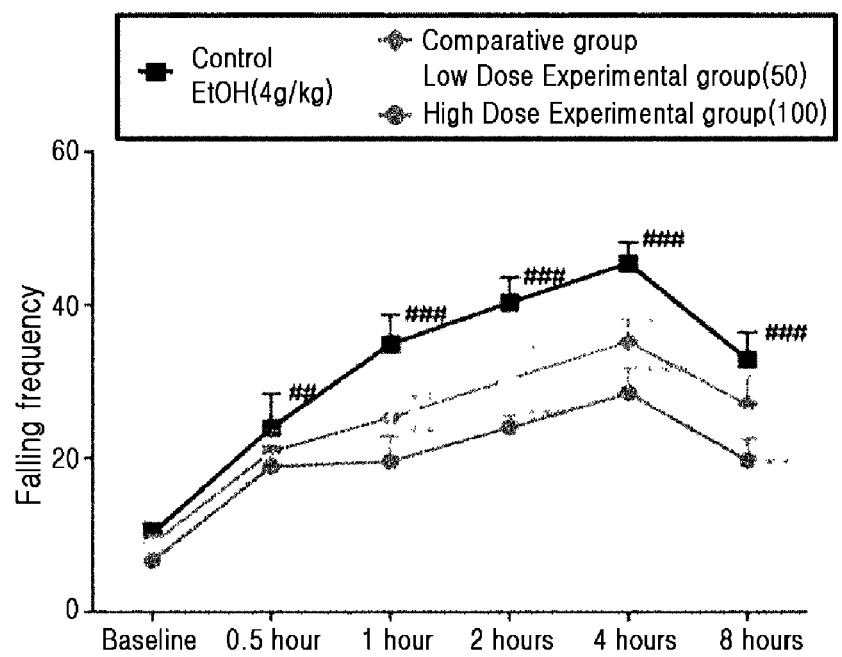
Figure 13C:
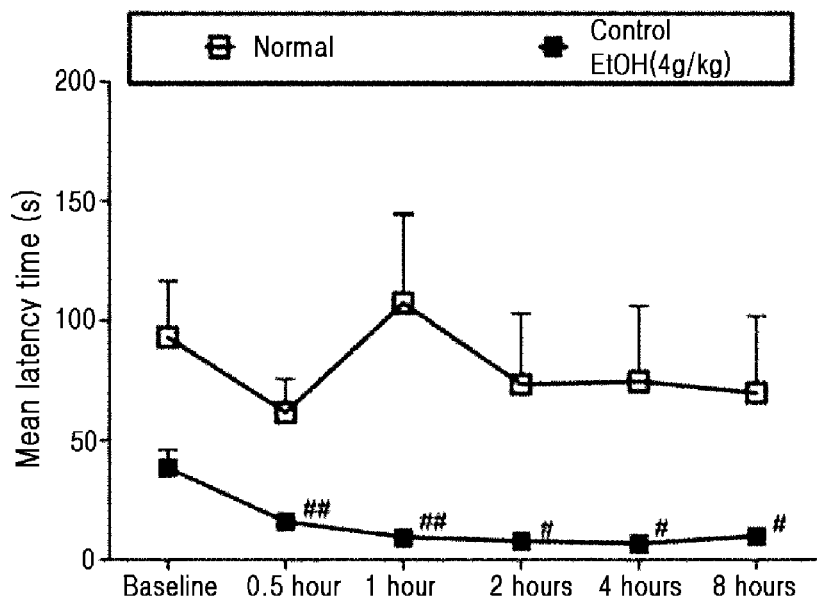
Figure 13C:
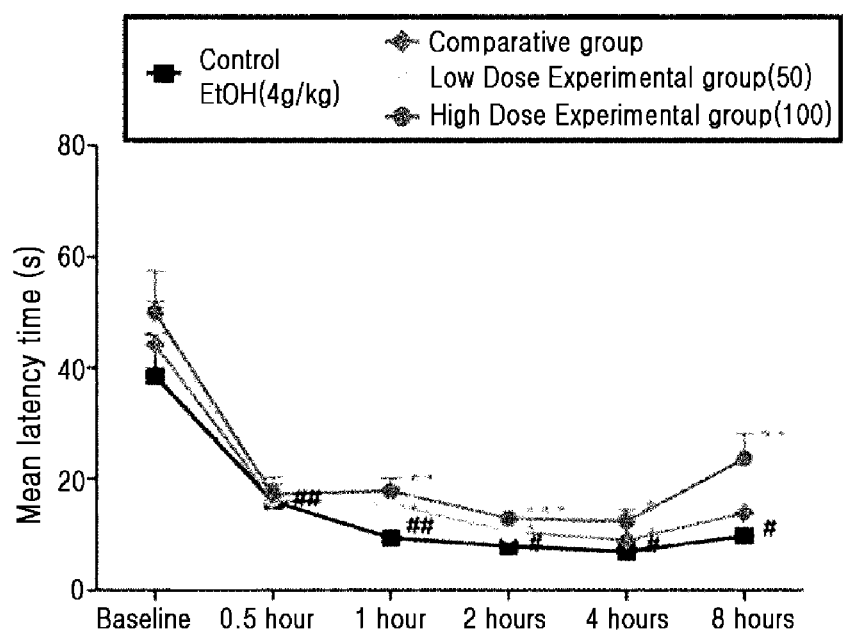
Figure 14A:
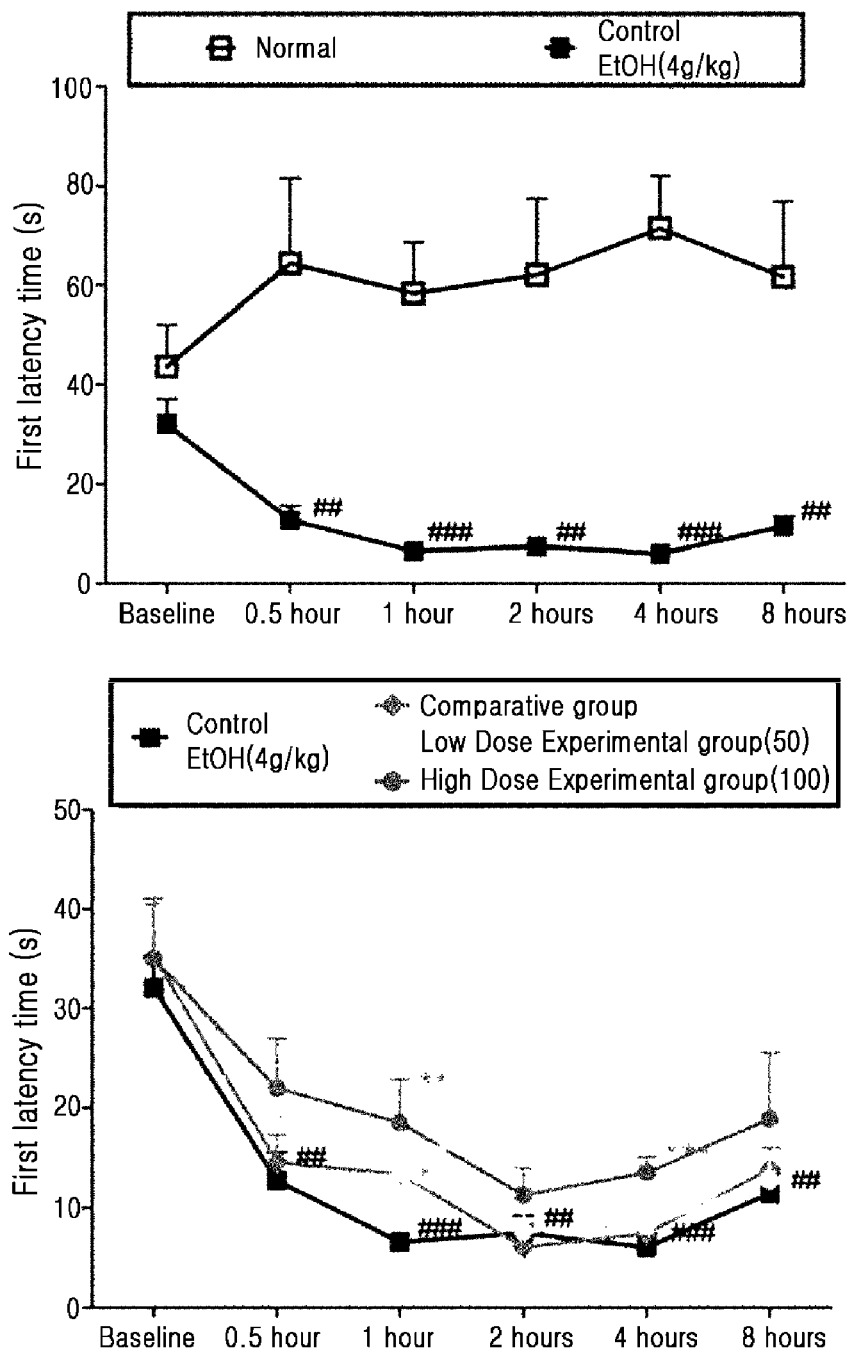
FIG. 14 is a graph showing motor activity on a wire, in which an alcohol-treated animal after treatment of a control group (non-composition-treated group; EtOH-treated group), low dose (50%) and high dose (100%) experimental groups (experimental composition-treated group) and a comparative group (comparative composition-treated group) was placed on an apparatus and (A) first latency time, (B) falling frequency, and (C) mean latency time were measured (Mean±SEM, n=10/## p<0.01 and ### p<0.001 versus Normal group/*p<0.05,  p<0.01 and * p<0.001 versus EtOH-treated group)
Figure 14B:
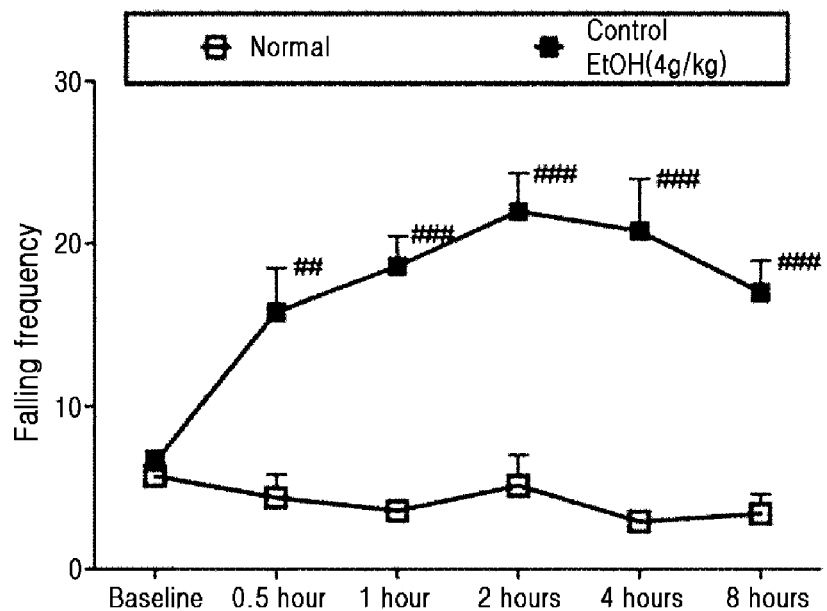
Figure 14B:
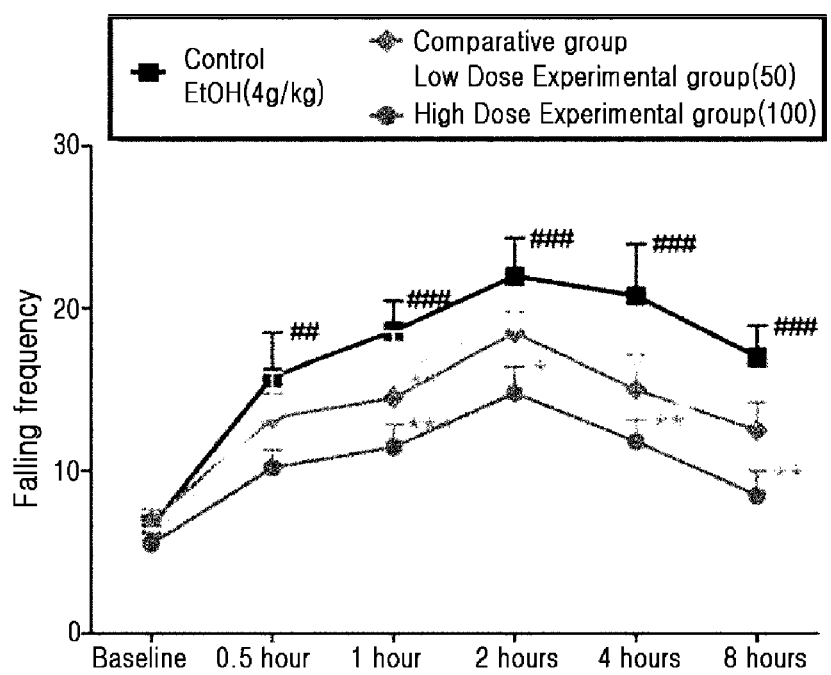
Figure 14C:
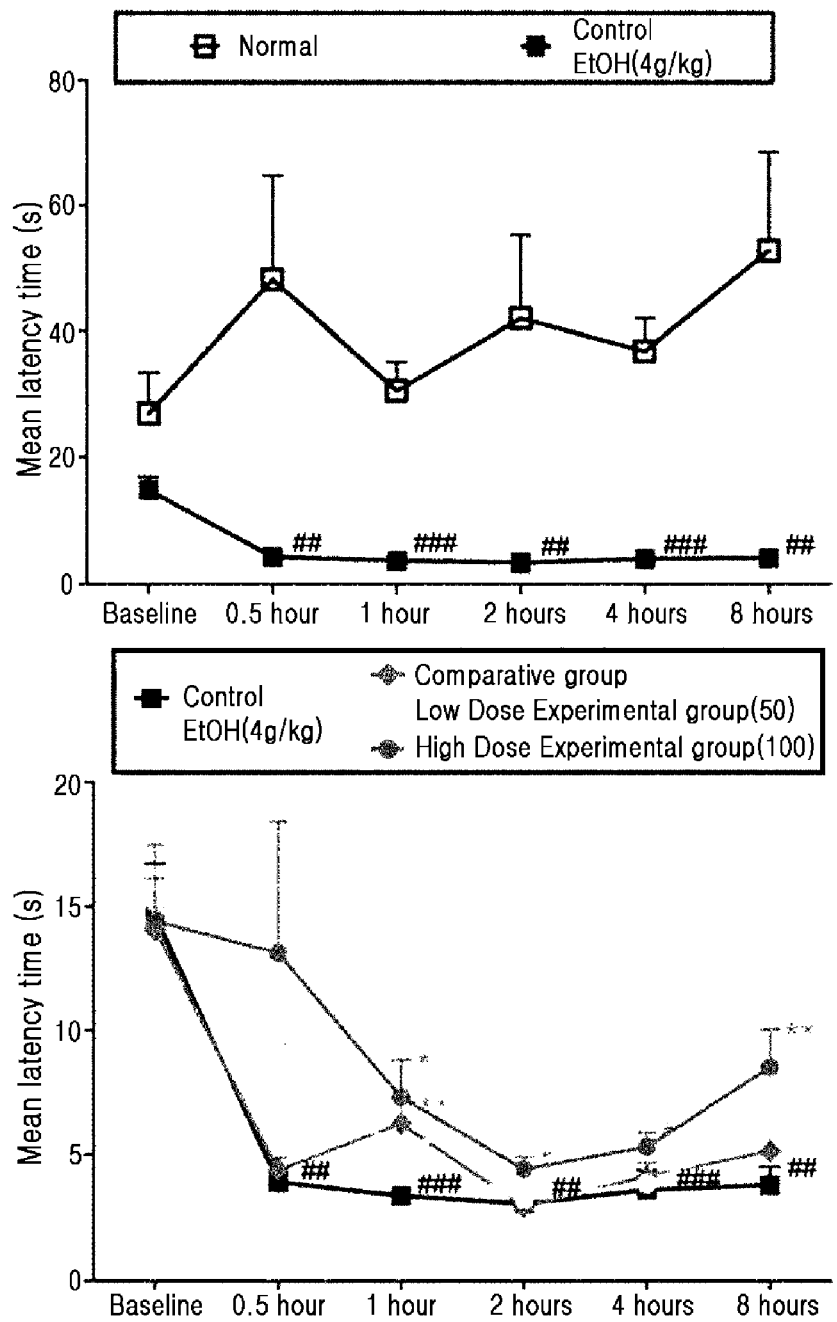

As shown in FIG. 12, the overall motor activity was significantly reduced from 30 minutes after alcohol administration. It was found that total movement distance and total movement duration of the experimental group were increased, compared to the control group, and a significant difference in the overall motor activity was observed from 2 hours after alcohol administration in the high dose (100%) experimental group, compared to the control group.

3-2-2. Measurement of Motor Activity on Rota-Rod

Animals were stabilized for 1 week, and they were trained for 5 minutes twice 2 days before the experiment and once one day before the experiment in the same manner as in Experimental Example 1-2-2. The experimental composition and the comparative composition prepared in Example 2 were administered to rats of low dose (50%) and high dose (100%) experimental groups and comparative group, respectively. The rats were divided into Experimental groups A, B, C, D, and Compositions A, B, C, D were orally administered to the rats. 30 minutes after administration, the rats were orally administered with ethyl alcohol. After 30 minutes, 1, 2, 4, and 8 hours from this baseline, the rats were placed on the apparatus, and then first latency time to fall (A), falling frequency (B) and mean latency time (C) were measured for 5 minutes. [Mean latency time=300 (s)/Falling frequency+1]

As shown in FIG. 13, when alcohol was administered, the latency time was shortened and the falling frequency was increased. The experimental group showed an increase in the motor activity which had been reduced by alcohol administration, compared to the control group. In particular, the high dose (100%) experimental group showed the highest effect of recovering motor activity, compared to the control group.

3-2-3. Measurement of Motor Activity on Wire

Animals were stabilized for 1 week, and they were trained in the apparatus twice for 2 days before the experiment (total 3 minutes; 1 minute for first time, 2 minutes for second time) in the same manner as in Experimental Example 1-2-3. The experimental composition and comparative composition prepared in Example 2 were administered to rats of low dose (50%) and high dose (100%) experimental groups and comparative group, respectively. The rats were divided into Experimental groups A, B, C, D, and Compositions A, B, C, D were orally administered to the rats. 30 minutes after administration, the rats were orally administered with ethyl alcohol. After 30 minutes, 1, 2, 4, and 8 hours from this baseline, the rats were placed on the apparatus, and then first latency time to fall (A), falling frequency (B) and mean latency time (C) were measured for 2 minutes.

As shown in FIG. 14, when alcohol was administered, the latency time was shortened and the falling frequency was increased. The experimental group showed an increase in the motor activity which had been reduced by alcohol administration, compared to the control group, and a significant difference in the motor activity, compared to the control group. In addition, the high dose (100%) experimental group showed the most excellent effect of recovering the motor activity which was reduced by alcohol administration.

3-2-4. Cold Swimming Test

In the same manner as in Experimental Example 1-2-4, the experimental composition and comparative composition prepared in Example 2 were administered to rats of low dose (50%) and high dose (100%) experimental groups and comparative group, respectively. The rats were divided into Experimental groups A, B, C, D, and Compositions A, B, C, D were orally administered to the rats. 30 minutes after administration, the rats were orally administered with ethyl alcohol. After 30 minutes, 1, 2, 4, and 8 hours from this baseline, the rats were allowed to swim in a cold pool and the latency time to give up swimming (up to 10 minutes) was measured.

Figure 15:
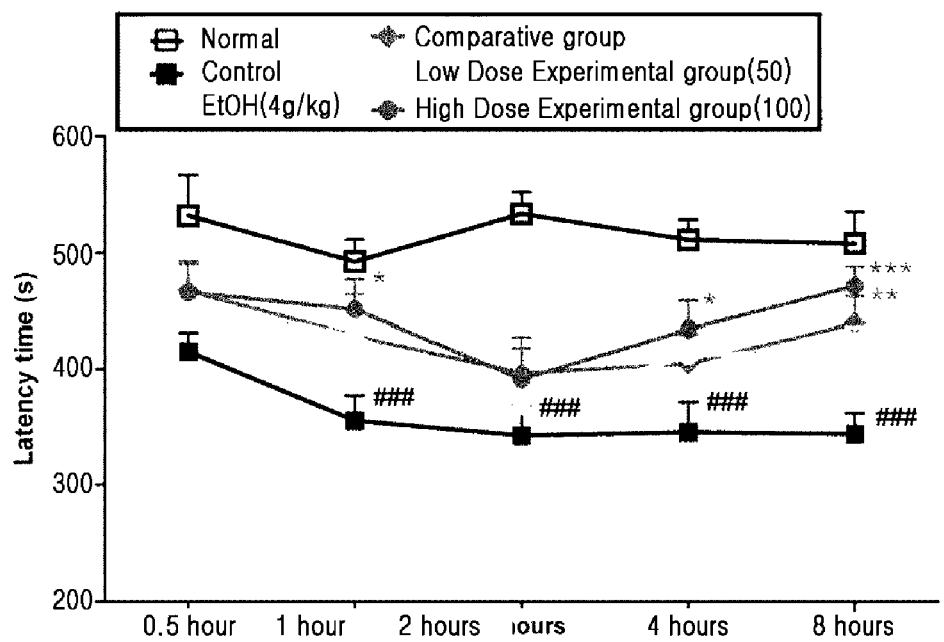
FIG. 15 is a graph showing cold swimming ability, in which an alcohol-treated animal after treatment of a control group (non-composition-treated group; EtOH-treated group), low dose (50%) and high dose (100%) experimental groups (experimental composition-treated group) and a comparative group (comparative composition-treated group) was allowed to swim in a cold pool and the latency time before giving up swimming was measured (Mean±SEM, n=10/### p<0.001 versus Normal group/ *p<0.05,  p<0.01 and * p<0.001 versus EtOH-treated group).

As shown in FIG. 15, when alcohol was administered, the ability to control body temperature and the motor activity were reduced, and thus cold swimming ability was significantly reduced. Improvement of the experimental group was more excellent than that of the control group. In particular, the high dose (100%) experimental group showed the highest effect of recovering the cold swimming ability from 4 hours after alcohol administration, compared to the control group.

Taken together, the composition comprising the *Laurus nobilis* leaf extract according to the present invention showed a remarkably excellent effect of lowering blood concentrations of alcohol and acetaldehyde. Further, 4 types of behavioral tests, in addition to analysis of blood concentrations of alcohol and acetaldehyde, were performed to confirm that the composition according to the present invention has an effect of relieving and preventing hangover, and the effect depends on the dose of the corresponding composition.

Although specific parts of the present invention have been described in detail, it will be apparent to those skilled in the art that these specific descriptions are provided for preferred embodiment and the scope of the present invention is not limited thereby. Therefore, the scope of the present invention should be defined only by the accompanying claims and equivalents thereof.

The invention claimed is:

1. A composition for preventing or treating hangover, comprising a *Laurus nobilis* leaf extract, an *Opuntia ficus indica* extract and a *Rosa roxburghii* extract as active ingredients, wherein a weight ratio of the *Laurus nobilis* leaf extract, the *Opuntia ficus indica* extract, and the *Rosa roxburghii* extract is 0.25 to 1 : 0.5 to 2 : 0.5 to 2.

2. The composition according to claim 1, further comprising an *Engelhardtia chrysolepis* HANCE extract, a *Nelumbo nucifera* seed extract, a *Hovenia dulcis* fruit extract or a mixture thereof.

3. The composition according to claim 1 or 2, wherein the composition is in the formulation of a solution, a suspension, a powder, a granule, a tablet, a capsule, a pill or an extract.

4. A food composition for preventing or relieving hangover, comprising a *Laurus nobilis* leaf extract, an *Opuntia ficus indica* extract and a *Rosa roxburghii* extract as active ingredients,
wherein a weight ratio of the *Laurus nobilis* leaf extract, the *Opuntia ficus indica* extract, and the *Rosa roxburghii* extract is 0.25 to 1 : 0.5 to 2 : 0.5 to 2.

5. The food composition according to claim 4 wherein the composition is in the form of a tea, a jelly, or a drink.

\* \* \* \* \*